(12) United States Patent
Huembelin et al.

(10) Patent No.: US 7,435,571 B2
(45) Date of Patent: Oct. 14, 2008

(54) MICROBIAL PRODUCTION OF COQ10

(75) Inventors: Markus Huembelin, Basel (CH); Rual Lopez-Ulibarri, Sisseln (CH); John B. Perkins, Reading, MA (US); Ghislain Schyns, Aesch (CH)

(73) Assignee: DSM IP Assets B.V., Heerlen (NL)

( * ) Notice: Subject to any disclaimer, the term of this patent is extended or adjusted under 35 U.S.C. 154(b) by 324 days.

(21) Appl. No.: 10/546,109

(22) PCT Filed: Feb. 13, 2004

(86) PCT No.: PCT/EP2004/001380

§ 371 (c)(1),
(2), (4) Date: Aug. 18, 2005

(87) PCT Pub. No.: WO2004/074487

PCT Pub. Date: Sep. 2, 2004

(65) Prior Publication Data

US 2006/0088920 A1    Apr. 27, 2006

(51) Int. Cl.
- *C12N 9/12* (2006.01)
- *C12N 9/10* (2006.01)
- *C12N 15/00* (2006.01)
- *C12N 1/20* (2006.01)
- *C07H 21/04* (2006.01)

(52) U.S. Cl. .................. 435/193; 435/194; 435/320.1; 435/252.3; 536/23.2

(58) Field of Classification Search ................. 435/194, 435/193, 320.1, 252.3; 536/32.2
See application file for complete search history.

(56) References Cited

U.S. PATENT DOCUMENTS 3,891,504 A    6/1975    Schocher et al.

FOREIGN PATENT DOCUMENTS

EP    1 227 155 A1    7/2002

OTHER PUBLICATIONS

Humbelin M. et al., Genetic of isoprenoid biosynthesis in Paracoccus zeaxanthinifaciens, Gene, 2000, 297, 129-139.*
Hümbelin et al., "*Decaprenyl Diphosphate Synthase (EC 2.1.1.31)*," EBI Database Accession No. Q8L116.
Hümbelin et al., "Genetics Of Isoprenoid Biosynthesis In Paracoccus Zeaxanthinifaciens," *Gene*, vol. 297, pp. 129-139 (2002).
Huembelin et al., "*Paracoccus Zeaxanthinifaciens phaA gene, phaB gene, ORFI and ddsA Gene*," EBI Database Accession No. AJ431695, XP002281316.

* cited by examiner

*Primary Examiner*—Nashaat T. Nashed
*Assistant Examiner*—Malgorzata A Walicka
(74) *Attorney, Agent, or Firm*—Bryan Cave LLP

(57) ABSTRACT

The present Invention relates to enzymes involved in the Synthesis of Coenzyme Q-10, i.e., decaprenyl diphosphate (DPP) synthase and 4-hydroxybenzoate polyprenyltransferase, to isolated DNA encoding said enzymes and to methods for the microbial production of Coenzyme Q-10.

12 Claims, No Drawings

MICROBIAL PRODUCTION OF COQ10

This application is the National Stage of International Application No. PCT/EP2004/001380, filed Feb. 13, 2004.

The present invention relates to enzymes involved in the synthesis of Coenzyme Q-10, to isolated DNA encoding said enzymes and to methods for the microbial production of Coenzyme Q-10.

Coenzyme Q-10 is found in microorganisms and plants, as well as in animals. There is established and growing evidence that Coenzyme Q-10 is an important factor in health and disease in humans. It can be produced by chemical synthesis or by fermentation using microorganisms.

The enzymes decaprenyl diphosphate (DPP) synthase and 4-hydroxybenzoate polyprenyltransferase catalyze steps in the biosynthesis of Coenzyme Q-10 (2,3-dimethoxy-dimethyl-6-decaprenyl-1,4-benzoquinone), also known as ubiquinone-10. The DPP synthase forms DPP by seven sequential additions of isopentenyl diphosphate (IPP) molecules to the isoprenoid intermediate farnesyl diphosphate (FPP). DPP is then coupled with 4-hydroxybenzoate, which is derived from chorismate in most if not all bacteria. This prenylation, which is catalyzed by 4-hydroxybenzoate polyprenyltransferase, results in 3-decaprenyl-4-hydroxybenzoate (3DP4HP). The aromatic ring of 3DP4HP is further modified to form ubiquinol, the reduced form of ubiquinone.

The isoprenoid intermediate IPP is synthesized by a multi-step catalytical pathway starting from acetyl-CoA. The enzyme acetyl-CoA acetyltransferase, which is encoded by phaA, catalyzes the condensation of two molecules of acetyl-CoA to form acetoacetyl-CoA, which is the first step in the synthesis of IPP. Acetoacetyl-CoA also serves as the substrate for the phaB gene product, acetoacetyl-CoA reductase, which catalyzes the first committed step in poly-hydroxyalkanoate (PHA) biosynthesis. In many bacteria the genes involved in PHA biosynthesis are grouped in operons. In *Paracoccus denitrificans* the phaA and phaB genes, encoding the acetyl-CoA acetyltransferase and acetoacetyl-CoA reductase, respectively, are clustered in an operon while phaC, the gene encoding the last enzyme in the pathway, PHA synthase, is not part of this operon.

The present invention is directed to an isolated DNA comprising (1) a nucleotide sequence that encodes decaprenyl diphosphate (DPP) synthase and (2) a nucleotide sequence that encodes 4-hydroxybenzoate polyprenyltransferase, wherein the nucleotide sequence encoding DPP synthase is selected from the group consisting of:

(a) a DNA sequence identified by SEQ ID NO: 16 or the complementary strand thereof,
(b) a DNA sequence which hybridizes under standard conditions to the DNA sequence defined in (a) or a fragment thereof, and encodes a polypeptide having the activity of DPP synthase;
(c) a DNA sequence which is at least 80%, preferably at least 90%, identical to a DNA which codes for a polypeptide represented by SEQ ID NO: 17 and encodes a polypeptide having the activity of DPP synthase; and
(d) a DNA sequence which codes for a polypeptide which is at least 80% identical to the amino acid sequence represented by SEQ ID NO: 17, and encodes a polypeptide having the activity of DPP synthase; and
wherein the nucleotide sequence encoding 4-hydroxybenzoate polyprenyltransferase is selected from the group consisting of:
(a') a DNA sequence identified by SEQ ID NO: 23 or the complementary strand thereof,
(b') a DNA sequence which hybridizes under standard conditions to the DNA sequence defined in (a') or a fragment thereof, and encodes a polypeptide having the activity of 4-hydroxybenzoate polyprenyltransferase;
(c') a DNA sequence which is at least 80%, preferably at least 90%, identical to a DNA which codes for a polypeptide represented by SEQ ID NO: 24, and encodes a polypeptide having the activity of 4-hydroxybenzoate polyprenyltransferase; and
(d') a DNA sequence which codes for a polypeptide which is at least 80% identical to the amino acid sequence represented by SEQ ID NO: 24, and encodes a polypeptide having the activity of 4-hydroxybenzoate polyprenyltransferase.

As uses herein, hybridizing under "standard conditions" means hybridization under stringent conditions as described, e.g., in Sambrook et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the sequences complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short hybridization probes (e.g. 10 to 50 nucleotides) and at least about 60° C. for long hybridization probes (e.g. greater than 50 nucleotides). Stringent conditions may also be achieved with the addition of destabilizing agents such as formamide. For the purposes of this disclosure, suitable stringent conditions for such hybridizations are those which include hybridization in a buffer of 40% formamide, 1M NaCl, 1% sodium dodecyl sulfate (SDS) at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

As used herein, the term "fragment" refers to nucleic acid sequences with a length of about 10 nucleotides or more.

As used herein, two nucleic acid sequences or polypeptides are said to be "identical" if the sequence of nucleotides or amino acid residues, respectively, in the two sequences is the same when aligned for maximum correspondence as described below. The terms "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using a sequence comparison algorithms as known in the art or by manual alignment and visual inspection. When percentage of sequence identity is used in reference to proteins or peptides, it is recognized that residue positions that are not identical often differ by conservative amino add substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988), e.g., as implemented in the program PC/GENE (Intelligenetics, Mountain View, Calif., USA). There may be gaps of non-identical nucleotides or amino acid residues among identical sequences. A nucleotide or amino acid sequence is included within the scope of the invention if it differs by a modification that reduces or alters the biological activity of one domain of a multi-domain enzyme, while preserving a second biological activity in a second domain of the enzyme. Generally, a polypeptide is considered to be within the scope of this invention if it is at least 80% identical to the naturally occurring amino acid sequence of DPP synthase or 4-hydroxybenzoate polyprenyltransferase as of SEQ ID NO: 17 or SEQ ID NO: 24. A nucleic add sequence is considered to be within the scope of this invention if it is at least 80%, preferably at least 90%, identical to a naturally occurring nucleic acid sequence encoding a DPP synthase or 4-hydroxybenzoate polyprenyltransferase as of SEQ ID NO: 16 or SEQ ID NO: 23.

Furthermore, the present invention is directed to a polypeptide comprising (1) a polypeptide having the amino acid sequence SEQ ID NO: 17, or an amino acid sequence having one or a few amino acid deletion(s), addition(s) or insertion(s) in SEQ ID NO: 17 and having DPP synthase activity, and (2) a polypeptide having the amino acid sequence SEQ ID NO: 24, or an amino acid sequence having one or a few amino acid deletion(s), addition(s) or deletion(s) in SEQ ID NO: 24 and having 4-hydroxybenzoate polyprenyltransferase activity.

As used herein, the term "one or a few amino acid deletion(s), addition(s) or insertion(s)" means that the respective polypeptide sequence is mutated by 1 or more deletion(s), addition(s) or insertion(s). In the context of the present application, the term "a few" means 2 or more.

The present invention further provides a construct comprising the novel nucleotide sequences as of the present invention and may also comprise regulatory sequences.

As used herein, a "construct" is a segment or sequence of DNA having inserted or added additional DNA, such as an expression vector or plasmid carrying a DNA insert. Such "additional DNA" is a DNA which is not naturally occurring at this position and which is inserted or added by cloning methods known in the art. Also included is a DNA sequence which is inserted into the genome of a microorganism by standard DNA transformation, transduction, or conjugation methods known by those skilled in the art. Thus, a construct as used in the context of the present invention includes the DNA sequences as disclosed herein inserted into a plasmid or expression vector or into the genome of a microorganism by methods known in the art. Suitable plasmids and expression vectors are known to those skilled in the art.

The term "regulatory sequences" includes sequences which control or mediate the transcription of the coding DNA. Such sequences maybe adjacent to the coding DNA or maybe located upstream or downstream from the coding DNA. Regulatory sequences include, but are not limited to, promoters, transcription modulators, ribosome binding sites, terminators, mRNA stabilizing sequences, and translation or transcription enhancer elements.

In one embodiment of the present invention, a microorganism is provided comprising a DNA as specified above. Thus, the present invention provides a microorganism comprising a construct as above. The microorganism is preferably a bacterium or yeast, more preferably a bacterium or yeast which is a natural producer of Coenzyme Q-10, such as *Gluconobacter* sp., *Sphingomonas trueperi*, *Schizosaccharomyces pombe*, *Candida* sp., *Pseudomonas* sp., or *Paracoccus denitrificans*. Most preferably is a bacterium of the species *Paracoccus zeaxanthinifaciens* or *Rhodobacter sphaeroides*.

The present invention provides a method or a process for the production of Coenzyme Q-10 in a microorganism comprising the steps of:
(a) increasing the expression of a gene coding for a protein having DPP synthase and/or a gene coding for a protein having 4-hydroxybenzoate polyprenyltransferase in order to increase the activity of said proteins, and
(b) culturing the microorganism or the host cell in a medium and under conditions where Coenzyme Q-10 is produced. The gene coding for DPP synthase is known as ddsA, the gene coding for 4-hydroxybenzoate polyprenyltransferase is known as ubiA. In one aspect, the process further comprises the step of eliminating geranyl geranyl diphosphate (GGPP) synthase activity by mutating the crtE gene in said microorganism.

The activity of an enzyme as of the present invention can be increased by methods including, but not limited to, increasing the copy number of the gene(s), using stronger promoter(s), stabilizing the mRNA(s), enhancing the translation, using mutant form(s) of the enzyme(s) with increased activity and/or increased stability and/or resistance to inhibition and/or resistance to substrate or product inhibition compared to the wildtype, or by any other means known to the skilled person in the art.

The medium and conditions for Coenzyme Q-10 productions are known to the skilled person, and are in detail described in the section of culture media and conditions in Example 1.

The term "mutation" or "mutating" is used interchangeably herein with modification to mean a change in the native nucleotide sequence that causes a corresponding change in the amino acids sequence of a protein. Such a change can cause a change such as in the function or activity of the protein. A mutation can be caused in a variety of ways including one or more frame shifts, substitutions, insertions and/or deletions, including nonsense mutations [amber (T/UAG), ocher (T/UAA) and opal (T/UGA)]. The deletion can be of a single nucleotide or more, including deletion of the entire gene. Methods to generate such mutation include, but are not limited to, chemical mutagenesis using NTG (N-methyl-N'-nitro-N-nitrosoguanidine) or EMS (ethylmethane sulfonate), and nitrous acid, UV (ultraviolet) irradiation, and mutagenesis using biological agents such as transposons, insertion elements, or specific genes that control mutation rates of a cell (e.g. mutS and mutT). Mutations can also be generated by DNA recombinant methods that employ preparation of DNA fragments containing a mutations generated by PCR and introducing such mutation-containing DNA fragment into the chromosome (at the native locus or at a second chromosomal site) by standard DNA transformation, transduction, or conjugation methods known by those skilled in the art.

It is a particular embodiment of the present invention to provide an isolated DNA selected from a DNA comprising a nucleotide sequence that encodes decaprenyl diphosphate (DPP) synthase, selected from the group consisting of:
(a) a DNA sequence identified by SEQ ID NO: 16 or the complementary strand thereof,
(b) a DNA sequence which hybridizes under standard conditions to the DNA sequence complementary to the DNA sequence defined in (a) or a fragment thereof, and encodes a polypeptide having the activity of decaprenyl diphosphate (DPP) synthase;
(c) a DNA sequence which codes for a polypeptide having the amino acid sequence encoded by the DNA sequence of (a) or (b);
(d) a DNA sequence which is identical to the extent of at least 80% to a DNA which codes for a polypeptide which comprises the amino acid sequence of SEQ ID NO: 17, and encodes a polypeptide having the activity of decaprenyl diphosphate (DPP) synthase; and
(e) a DNA sequence which codes for a polypeptide which comprises an amino acid sequence which is identical to the extent of at least 80% to the amino acid sequence of SEQ ID NO: 17, and encodes a polypeptide having the activity of decaprenyl diphosphate (DPP) synthase; and
a DNA comprising a nucleotide sequence that encodes 4-hydroxybenzoate polyprenyltransferase, selected from the group consisting of:
(a') a DNA sequence identified by SEQ ID NO: 23 or the complementary strand thereof,
(b') a DNA sequence which hybridizes under standard conditions to the DNA sequence complementary to the DNA sequence defined in (a') or a fragment thereof, and encodes a polypeptide having the activity of 4-hydroxybenzoate polyprenyltransferase;
(c') a DNA sequence which codes for a polypeptide having the amino acid sequence encoded by the DNA sequence of (a') or (b');
(d') a DNA sequence which is identical to the extent of at least 80% to a DNA which codes for a polypeptide which comprises the amino acid sequence of SEQ ID NO: 24, and encodes a polypeptide having the activity of 4-hydroxybenzoate polyprenyltransferase; and
(e') a DNA sequence which codes for a polypeptide which comprises an amino acid sequence which is identical to the extent of at least 80% to the amino acid sequence of SEQ ID NO: 24, and encodes a polypeptide having the activity of 4-hydroxybenzoate polyprenyltransferase.

In a further embodiment, the present invention includes a method for the production of Coenzyme Q-10 in a microorganism comprising increasing the expression of a gene selected from ddsA and ubiA to increase the activity of enzymes selected from DPP synthase and 4-hydroxybenzoate polyprenyltransferase, and culturing the cell in a medium and under conditions where Coenzyme Q-10 is produced.

The following examples are provided to further illustrate the process of the present invention. These examples are illustrative only and are not intended to limit the scope of the invention in anyway.

EXAMPLE 1

Bacterial Strains, Microbiological Methods and Analytical Procedures

In bacteria including *Paracoccus zeaxanthinifaciens* the synthesis of zeaxanthin from the isoprenoid intermediates FPP and IPP involves five enzymatic steps. First, geranyl geranyl diphosphate (GGPP) is formed by GGPP synthase which is encoded by crtE. Then, two GGPP molecules are combined to form phytoene, catalyzed by the crtB encoded enzyme phytoene synthase. The next enzyme, lycopene synthase, which is encoded by crtI, converts phytoene into lycopene by carrying out four desaturation steps. Lycopene cyclase, encoded by crtY, converts lycopene into β-carotene which is then hydroxylated by the crtZ encoded enzyme β-carotene hydroxylase, resulting in zeaxanthin. Lycopene, β-carotene and zeaxanthin are red or orange whereas the other intermediates are colorless.

*P. zeaxanthinifaciens* strain ATCC 21588, available from the American Type Culture Collection (ATCC), 10801 University Blvd., Manassas Va. 20110-2201, USA, is a wild-type, marine zeaxanthin-producing bacterium (U.S. Pat. No. 3,891,504). Strains R1534 and R114 are improved zeaxanthin-producing mutants derived from ATCC 21588 by classical mutagenesis and screening procedures. Strains R1534 and R114 were previously deposited at the ATCC according to the terms of the Budapest Treaty and have been assigned the ATCC strain numbers PTA-3336 and PTA-3335, respectively. The construction of strains R1534intE, UV9-4 and EMS9-7 is described in detail in Example 2.

Culture Media and Conditions

*E. coli* strains were grown at 37° C. in LB medium (Becton Dickinson, Sparks, Md., USA). For maintenance of plasmids in recombinant strains, ampicillin (100 μg/ml) and/or kanamycin (25-50 μg/ml, depending on the experiment) were added to the culture medium. Agar (1.5% final concentration) was added for solid media. Liquid cultures were grown in a rotary shaker at 200 rpm.

*P. zeaxanthinifaciens* strains were grown at 28° C. The compositions of the media used for *P. zeaxanthinifaciens* are described below (the exact medium used for each experiment is specified in the later Examples). All liquid cultures of *P. zeaxanthinifacieis* grown in flasks were shaken in a rotary shaker at 200 rpm unless specified otherwise. Agar (1.5% final concentration) was added for solid medium. When media were sterilized by autoclaving, the glucose was added (as a concentrated stock solution) after sterilization to achieve the desired final concentration.

F-Medium contains (per liter distilled water): tryptone, 10 g; yeast extract, 10 g; NaCl, 30 g; D-glucose.$H_2O$, 10 g; $MgSO_4.7H_2O$, 5 g. The pH is adjusted to 7.0 before sterilization by filtration or autoclaving.

Medium 362F/2 contains (per liter distilled water): D-glucose.$H_2O$, 33 g; yeast extract, 10 g; tryptone, 10 g; NaCl, 5 g; $MgSO_4.7H_2O$, 2.5 g. The pH of the medium is adjusted to 7.4 before sterilization by filtration or autoclaving. Following sterilization, 2.5 ml each of microelements solution, NKP solution and CaFe solution are added. The latter three solutions are sterilized by filtration. Microelements solution contains (per liter distilled water): $(NH_4)_2Fe(SO4)_2.6H_2O$, 80 g; $ZnSO_4.7H_2O$, 6 g; $MnSO_4.H_2O$, 2 g; $NiSO_4.6H_2O$, 0.2 g; EDTA, 6 g. NKP solution contains (per liter distilled water):$K_2HPO_4$, 250 g; $(NH_4)_2PO_4$, 300 g. CaFe solution contains (per liter distilled water): $CaCl_2.2H_2O$, 75 g; $FeCl_3.6H_2O$, 5 g; concentrated HCl, 3.75 ml.

Fed-batch Cultivation of *P. zeaxanthinifaciens* Strains

All cultures were initiated from frozen cell suspensions (stored as 15-20% glycerol stocks at −80° C.). The precultures for the fed-batch fermentations were prepared in duplicate 2 liter baffled shake flasks containing 200 ml of 362F/2 medium each. One milliliter of thawed cell suspension was used as inoculum for each flask. The initial pH of the precultures was 7.2. The precultures were incubated at 28° C. with shaking at 250 rpm for 28 hours, after which time the optical density at 660 nm ($OD_{660}$) was between 14 and 22 absorbance units, depending on the strain used. Main cultures were grown in Biostat ED Bioreactors (B. Braun Biotech International, Melsungen Germany) containing medium having the following composition (per liter distilled water): D-glucose.$H_2O$, 25 g; yeast extract (Tastone 900), 17 g; NaCl, 4.0 g; $MgSO_4.7H_2O$, 6.25 g; $(NH_4)_2Fe(SO_4)_2.6H_2O$, 0.5 g; $ZnSO_4.7H_2O$, 0.038 g; $MnSO_4.H_2O$, 0.013 g; $NiSO_4.5H_2O$, 0.001 g; $CaCl_2.2H_2O$, 0.47 g; $FeCl_3.6H_2O$, 0.062 g; niacin, 0.01 g; $NH_4Cl$, 0.5 g; antifoam, 0.1 ml; KP solution, 3.5 ml. The composition of KP solution is (per liter distilled water): $K_2HPO_4$, 250 g; $NaH_2PO_4.2H_2O$, 200 g; $(NH_4)_2HPO_4$, 100 g. Kanamycin (50 mg/l final concentration) was added to the medium for plasmid-carrying strains. The feeding solution used in all processes had the following composition (per liter distilled water): D-glucose.$H_2O$, 550 g; KP solution, 18.25 ml. The initial volume in the bioreactor (after inoculation) was 8 L. Precultures were diluted as needed with sterile water such that addition of 50 ml to the bioreactor achieved an initial $OD_{660}$ value of 0.5. Fermentation conditions were automatically controlled as follows: 28° C., pH 7.2 (pH controlled with addition of 28% $NH_4OH$), dissolved oxygen controlled at a minimum of 40% relative value (in cascade with agitation), minimum agitation of 300 rpm and an aeration rate of 1 v.v.m. (relative to final volume). The cultivations proceeded under these conditions without addition of feed solution for about 20 hours (batch phase). After this time, a decrease in agitation speed, a sharp reduction of base consumption and a decrease in $CO_2$ production were the indication that the initial glucose was exhausted and the feeding was started. A standard feed profile was defined as follows (from feeding start point): ramp from 50 g/h to 80 g/h in 17 hours, continue at 80 g/h for 7 hours then ramp down to 55 g/h in 11 hours and continue at 55 g/h for the rest of the fermentation. The final volumes of the main cultures were about 10 liters.

Methods for Analyzing Coenzyme Q-10

Sample preparation and extraction. 20 ml of culture were transferred to a disposable 50 ml polypropylene centrifuge tube and centrifuged at 4000 rpm for 20 min. The supernatant was removed and discarded. The pellet was resuspended in 10 ml of acetone, and the samples were sonified for 20 seconds. The tubes were capped and the samples were mixed using an IKA Vibrax shaker for 20 min. The samples were then centrifuged at room temperature for 10 min at 4000 rpm, and the supernatant was transferred into a clean 50 ml polypropylene centrifuge tube. 10 ml of acetone and 10 ml of tert-butyl methyl ether (TBME) were added to the pellet to extract a second time. The sonication, mixing and centrifugation steps were repeated as for the first extraction. The supernatant from this second extraction was removed and combined with the supernatant of the first extraction. Five milliliters of ethanol was added to the combined extracts to facilitate the removal of water. After mixing the samples, the solvents were removed using a SpeedVac evaporator (ambient temperature). The residue was resolubilized in 1 ml of TBME plus 1 ml of ethanol. The samples were then sonified in an ultrasonic bath for 5 min to facilitate the dissolution. Finally, the samples were centrifuged and the supernatants transferred to amber glass vials for analysis by high performance liquid chromatography (HPLC).

HPLC. A reversed phase HPLC method was developed for the simultaneous determination of ubiquinones and their corresponding hydroquinones. The method is able to clearly separate the carotenoids phytoene, α-carotene, β-cryptoxanthin and zeaxanthin from Coenzyme Q-10. Chromatography was performed using an Agilent 1100 HPLC system equipped with a thermostatted autosampler and a diode array detector. The method parameters were as follows:

| Column: | YMC Carotenoid C30 column; 5 micron, steel, 250 mm × 4.6 mm I.D. (YMC, Part No. CT99S052546WT) |
|---|---|
| Guard column: | Pelliguard LC-18 cartridge, 20 mm (SUPELCO, Part No. 59654) |
| Mobile phase: | Mixture of acetonitrile:methanol:TBME (ratio 58%:10%:32%), isocratic elution |
| Run time: | 25 min |
| Typical column pressure: | 48 bar at start |
| Flow rate: | 1.0 ml/min |
| Detection: | UV at 280 nm |
| Injection volume: | 20 µl |
| Column temperature: | 15° C. |

Reagents. Acetonitrile and TBME were HPLC grade and were obtained from Fluka. Ethanol (p.a.) and methanol (Lichrosolv) was purchased from Merck, Darmstadt. Acetone (puriss., p.a.) and Coenzyme Q-10 were purchased from Fluka.

Calculations. Quantitative analyses were performed with a two level calibration using external standards. Calculations were based on peak areas.

Selectivity. The selectivity of the method was verified by injecting standard solutions of the relevant reference compounds. The target compounds (Coenzyme Q-10 and ubiquinol-10) were completely separated and showed no interference. The retention times of selected compounds are: all-trans-Zeaxanthin, 8.0 min; 15Z-Phytoene, 10.4 min; Coenzyme Q-9, 11.0 min; β-Cryptoxanthin, 12.3 min; ubiquinol-10, 13.8 min; Coenzyme Q-10, 14.8 min; β-Carotene, 19.0 min.

Linearity. A dilution series of Coenzyme Q-10 in TBME/ethanol (1:1) was prepared (final concentrations of 300, 100, 30 and 3 µg/ml) and analyzed by the HPLC method described above. A linear range was found from 3 µg/ml to 300 µg/ml. The correlation coefficient was 0.9999.

Limit of detection. The lower limit of detection for Coenzyme Q-10 by this HPLC method was determined to be 1 µg/ml.

EXAMPLE 2

Construction of crtE Mutants of P. zeaxanthinifaciens

Insertional inactivation of the crtE gene in P. zeaxanthinifaciens strain R1534. The cloning and sequencing of the crtE gene from P. zeaxanthinifaciens strain R1534 was reported by Pasamontes et al. [Gene 185:37-41 (1997)]. A crtE-specific DNA fragment having PstI restriction enzyme recognition sites at its 5' and 3' ends was created by polymerase chain reaction (PCR) using plasmid pRSF1010-Ampr-crt2 (U.S. Pat. No. 6,291,204) as the template. The forward and reverse primers used had the sequence as illustrated in SEQ ID NO: 1 and SEQ ID NO: 2, respectively. PCR reaction conditions were: 1 min at 94° C. (one cycle), 1 min at 94° C. followed by 1.5 min at 72° C. (30 cycles), 7 min at 72° C. (one cycle). The 460 base pair (bp) DNA fragment produced by the PCR reaction was digested with PstI and purified from an agarose gel using a QIAquick column (Qiagen, Hilden, Germany). The isolated fragment was ligated with the "suicide" plasmid vector pSUP202 [Simon et al., Bio/Technology 1:784-791 (1983)] that had been previously digested with PstI. The ligated mixture was used to transform *E. coli* S-17 cells using standard procedures. Screening of transformants confirmed the construction of the desired plasmid containing the internal fragment of crtE (designated plasmid pSUPcrtE). Plasmid pSUPcrtE was transferred to *P. zeaxanthinifaciens* strain R1534 using the conjugation method as disclosed in U.S. Pat. No. 6,291,204. Transconjugants were selected on F-agar medium containing 100 μg/ml rifampicin and 3 μg/ml tetracycline. Approximately $10^3$ colonies were obtained. The vast majority of these colonies showed a change in color (became white) compared to strain R1534 (yellow due to zeaxanthin production), consistent with the loss of zeaxanthin production due to insertional inactivation of the crtE gene.

Ten representative putative crtE integrants were selected for analysis by colony PCR as follows. A colony was transferred to a 1.5-ml microfuge tube. The sample was heated in a microwave oven (1 min at 900 watts) and then transferred to ice. A PCR mix was then added that contained PCR buffer, 15% glycerol, polymerase, nucleotides and primers. PCR conditions were: 1 min at 94° C. followed by 30 sec at 57° C. and 1 min at 72° C. (total 25 cycles), then 7 min at 72° C. (one cycle). The oligonucleotide primers used were designed so that a PCR product should be obtained only if the desired integration of the pSUPcrtE plasmid had occurred at the crtE locus in the *P. zeaxanthinifaciens* strain R1534 chromosome. The forward primer, pCrtEampF (SEQ ID NO: 3) was crtE-specific, while the reverse primer pCrtEampR (SEQ ID NO: 4) was bla (ampicillin resistance gene)-specific. Using this colony PCR method, it was found that 10 out of 10 colonies tested contained an integration of the suicide vector pSUPcrtE at the crtE locus (all gave a PCR product of the expected size). Moreover, using specially designed PCR primers corresponding to specific segments of the bla gene of vector pSUP202, it was determined that 8 out of 10 of the crtE integrants contained multiple copies of pSUPcrtE in head-to-tail orientation.

Three of the crtE integrants (and *P. zeaxanthinifaciens* R1534 as control) were further analyzed by Southern hybridization. The strains were grown in liquid F-medium and chromosomal DNA was extracted from the cells using standard methods. Samples of chromosomal DNA were digested with restriction enzymes AlwNI, XhoI, BglII, PvuII and BglII plus PvuII and subjected to agarose gel electrophoresis. Transfer of fragments to the membrane and hybridization with the probe were done according to standard procedures. The crtE gene from *P. zeaxanthinifaciens* R1534 was labeled with $^{32}P$ and used as a probe. In all hybridizations with digested chromosomal DNA from the control strain R1534, the number and size of the fragments that hybridized to the crtE probe was as expected based on the nucleotide sequence of the crtE gene isolated from the chromosome of R1534. The hybridization results with digested DNA from the three crtE integrants were significantly different from the results obtained for the R1534 control, and (as was the case with the colony PCR analysis), were consistent with integration of multiple copies of pSUPcrtE at the chromosomal crtE locus. One integrant, designated R1534intE (listed in Table 1), was saved for further experiments (described in Example 4).

Creation of crtE mutants of *P. zeaxanthinifaciens* strain R114. *P. zeaxanthinifaciens* strain R114 was mutagenized using standard procedures (treatment with ultraviolet [UV] irradiation or ethyl methane sulfonate [EMS]). Briefly, an overnight culture of strain R114 (grown in F-medium) was subcultured to an $OD_{660}$ of 0.1 and incubated with shaking for 3 hours. Aliquots of the culture were centrifuged, the cell pellets were washed by resuspending in 20 mM potassium phosphate buffer (pH 7.2), and the suspension was again centrifuged to collect the cells. The washed cell pellets were then resuspended to an $OD_{660}$ of 0.1 in 20 mM potassium phosphate buffer (pH 7.2). For UV mutagenesis, 10-ml aliquots of cell suspension were transferred to a 100-ml glass beaker. The suspension was continuously gently mixed on a magnetic stirrer (a paper clip was placed in the beaker). The mixing cell suspension was irradiated with UV light for a predetermined time at a flux of 1450 μW/cm². For EMS mutagenesis, 0.1 ml of EMS was added to a 10-ml aliquot of the washed cell suspension, and the mixture was shaken on a rotary shaker for up to 90 min. The cells were then collected by centrifugation, and washed twice to remove the mutagen.

Several preliminary experiments were done to optimize both mutagenesis procedures with respect to percent survival, dilutions for plating, etc. Once these conditions were established, UV- or EMS-mutagenized *P. zeaxanthinifaciens* strain R114 cells were plated on 362F/2 agar plates to isolate white (non-zeaxanthin-producing) colonies. Many such mutants were obtained and restreaked on 362F/2 agar plates for single colony isolation and confirmation of low/no reversion frequency. A total of 43 stable mutants were further evaluated as described in the following sections.

Mutations in the crtE, crtB or crtI genes of *P. zeaxanthinifaciens* would be expected to give rise to white colonies, because lycopene is the first intermediate in the zeaxanthin pathway that gives a visible color. To identify crtE mutants among the 43 white non-zeaxanthin-producing mutants of strain R114, a two-step screening approach was taken. First, the mutants were screened for phytoene accumulation, which is indicative of loss of activity of the crtI gene product, lycopene cyclase. Since phytoene production is not possible in a mutant blocked at crtE, any mutants that accumulate phytoene can be eliminated as being crtE mutants and therefore excluded from further consideration. Second, the non-phytoene-accumulating white mutants identified in the first step were transformed with plasmid pBBR-K-PcrtE-crtE$_{R114}$, which carries the cloned crtE gene from *P. zeaxanthinifaciens* strain R114, to test for genetic complementation. Restoration of zeaxanthin production (i.e., yellow colonies) upon introduction of the cloned crtE gene strongly indicates that the basis for the white colony phenotype is a mutation(s) in crtE that inactivates geranyl geranyl diphosphate (GGPP) synthase.

The mutants were tested for accumulation of phytoene in shake flask cultures. The white mutants (plus the parental control strain R114) were grown in 110 ml of 362F/2 medium in 500-ml baffled flasks. The initial $OD_{660}$ of the cultures was 0.16. At 24, 48 and 72 hours, 30-ml samples were removed, placed in 50-ml polypropylene tubes and centrifuged to collect the cells. The cell pellet was washed with water and recentrifuged. The final cell pellet was then analyzed for phytoene accumulation by HPLC using the same method described in Example 1 for analysis of Coenzyme Q-10. Since a standard for phytoene was not available, the peak in the chromatogram corresponding to phytoene was identified by its UV spectrum and by the mass of the compound determined by mass spectrometry. Phytoene concentration was estimated based on the ratio of the specific absorption coefficient of phytoene and Coenzyme Q-10. This method allowed clear discrimination of those mutants that accumulated phytoene in the shake flask cultures. Six mutants that did not accumulate phytoene (UV6-1, UV7-6, UV9-4, EMS3-6, EMS3-15 and EMS9-7) were carried forward to the next level of testing.

The test for genetic complementation of the 6 white, non-phytoene-accumulating mutants UV6-1, UV7-6, UV9-4, EMS3-6, EMS3-15 and EMS9-7 by the cloned crtE gene was done as follows. For each mutant, a volume of 1.5 ml of stationary phase culture was used to inoculate 100 ml of F-medium. The culture was grown at 28° C., 200 rpm until an $OD_{660}$ of about 0.5 was reached. The cells were then harvested by centrifugation at 7,000×g for 15 min at 4° C., and washed twice in 100 ml ice-cold 1 mM HEPES buffer, pH 7.0. The final pellet was resuspended in 0.1 ml of ice-cold 1 mM HEPES buffer, pH 7.0, and the now electrocompetent cells were either used immediately for electroporation, or glycerol was added to a final concentration of 15% and the cells were stored in 50 µl aliquots at −70° C. For transformation, 1-5 µl plasmid pBBR-K-PcrtE-crtE$_{R114}$ (in salt-free solution) was added to 0.1 ml of the electrocompetent cells, and electroporation was performed (conditions: 18 kV/cm and 129 ohms in ice-cooled 1-mm cuvettes; pulse lengths were typically between 4 and 5 milliseconds). One ml of F-medium was then added and the cell suspension was incubated for 1 hour at 28° C. with shaking. Dilutions of the suspension were then spread onto F-agar plates containing 50 µg/ml kanamycin, and the plates were incubated at 28° C.

All kanamycin resistant colonies (i.e., transformants) of mutants UV6-1, UV9-4, EMS3-6, and EMS9-7 were deep yellow in color, while transformants of mutants UV7-6 and EMS3-15 remained white. This genetic complementation test indicated that mutants UV6-1, UV9-4, EMS3-6, and EMS9-7 contain mutations in crtE that inactivate GGPP synthase. Mutants UV9-4 and EMS9-7 were used in further experiments to evaluate Coenzyme Q-10 production.

EXAMPLE 3

Cloning and Sequencing of the ddsA Genes from *P. zeaxanthinifaciens* Strains R114 and ATCC 21588

Methods

Isolation of genomic DNA. A 600-ml culture of *P. zeaxanthinifaciens* strain R114 (grown in F-medium) was centrifuged for 10 min at 10,000×g at 4° C. and the pellet was washed once with 200 ml lysis buffer (0.1M NaCl, 50 mM EDTA, 10 mM Tris-HCl, pH 7.5) and once with 100 ml lysis buffer. The final pellet was resuspended in 20 ml lysis buffer containing 50 mg lysozyme and 1 mg RNase A (DNase free). After incubation for 15 min at 37° C., 1.5 ml of 20% sodium N-lauroyl-sarcosinate and 2.25 mg of proteinase K were added. After incubation at 50° C. for 30-60 min the lysate was extracted with one volume of buffer-saturated phenol, pH 7.5-7.8 by gentle but thorough mixing. The emulsion was centrifuged for 20 min at 30,000×g and the aqueous phase was re-extracted with phenol. The phases were separated as before and the aqueous phase was extracted twice with one volume phenol:chloroform (1:1). At this step centrifugation for 20 min at 3,200×g in a swinging bucket rotor was sufficient to get satisfactory phase separation. After a final extraction with one volume of chloroform, 0.1 volume of 3M sodium-acetate (pH 5.2) was added and the solution was overlaid with 2 volumes ice-cold ethanol. The precipitated DNA was spooled with a glass-rod, soaked in 70% ethanol for 5 min, rinsed with chloroform and then air dried for 5-10 min. The DNA was resuspended overnight in 5 ml TE buffer (10 mM Tris-HCl, pH 7.5, 1 mM EDTA). Since the solution was yellow due to traces of zeaxanthin, the organic extractions and the spooling were repeated as above to obtain a clear preparation.

λ-library. A custom made library with partially Sau3AI-digested *P. zeaxanthinifaciens* strain R114 DNA in lambda FIX® II was purchased from Stratagene (La Jolla, Calif., USA).

PCR. PCR was performed in a GeneAmp® PCR system 9700 (PE Applied Biosystems, Foster City, Calif., USA) using the GC-rich PCR system (Roche Molecular Biochemicals, Mannheim, Germany) according to the manufacturers instructions. Typically, the $MgCl_2$ concentration used was 1.5 mM and the resolution solution was added to a final concentration of 1M.

DNA Labeling and detection. The PCR DIG Probe Synthesis Kit and the DIG Luminescent Detection Kit were used for DNA labeling and detection, respectively (both obtained from Roche Molecular Biochemicals, Mannheim, Germany).

Isolation of λ-DNA. The Qiagen® Lambda Kit (Qiagen, Hilden, Germany) was used following the manufacturer's instructions.

DNA sequencing. Sequencing reactions were performed using the BigDye® DNA sequencing kit (PE Applied Biosystems, Foster City, Calif., USA) according to the manufacturer's instructions. Sequencing reaction products were purified on DyeEx™ spin columns (Qiagen, Hilden, Germany) and fragment separation and detection was done with an ABI Prism™ 310 Genetic Analyzer (PE Applied Biosystems, Foster City, Calif., USA).

Cloning and sequencing of the ddsA gene from *P. zeaxanthinifaciens* strain R114. The ddsA gene (coding for DPP synthase) of *P. zeaxanthinifaciens* strain R114 was initially identified fortuitously during the during and sequencing of the phaAB gene cluster. PCR fragments containing parts of phaA from *P. zeaxanthinifaciens* strain R1534 and phaC from *P. zeaxanthinifaciens* strain R114 were obtained using primers based on the *P. denitrificans* phaA and phaC gene sequences. The PCR fragments were then used to screen a *P. zeaxanthinifaciens* strain R114 λ-library for the phaA and phaC genes. From the library, DNA fragments hybridizing to the probes were identified and cloned. Sequencing confirmed that the phaA gene and the phaC gene were indeed located on the cloned fragments. In addition, the phaB gene was found to be located downstream of phaA. Therefore, as is the case in *P. denitrificans*, in *P. zeaxanthinifaciens* the phaA and phaB genes are clustered whereas the phaC gene is located elsewhere in the genome. Sequencing of the region downstream of phaAB revealed an open reading frame that was identified as the ddsA gene based on sequence similarity to the ddsA gene from *P. denitrificans*. The nucleotide sequence of the ddsA gene of *P. zeaxanthinifaciens* strain R114 (SEQ ID NO: 5) and the corresponding amino acid sequence of the DPP synthase it encodes (SEQ ID NO: 6) were deposited with EMBL on Feb. 21, 2002 and were made publicly available on May 2, 2002 under the accession number AJ431695.

Sequencing of the ddsA gene from *P. zeaxanthinifaciens* strain ATCC 21588. The forward primer 7R-01 (SEQ ID NO: 7) and reverse primer dds-3 (SEQ ID NO: 8) were used to amplify the ddsA gene using genomic DNA from *P. zeaxanthinifaciens* ATCC 21588 as template, and the PCR product was sequenced. Comparison of the ddsA sequences from the wild-type strain ATCC 21588 and its classically-derived mutant R114 revealed that the ddsA gene in R114 contains a G to A mutation in nucleotide 698 within the coding region. This changes the middle nucleotide (underlined) in codon 233 from GGC to GAC, which leads to the change of amino acid 233 from glycine (in ATCC 21588) to aspartate (in R114).

EXAMPLE 4

Effect of Overexpression of the *P. zeaxanthinifaciens* ddsA Genes on Coenzyme Q-10 Production in *P. zeaxanthinifaciens*

Cloning of the ddsA genes from *P. zeaxanthinifaciens* for overexpression in *P. zeaxanthinifaciens*. The coding region of the *P. zeaxanthinifaciens* strain R114 ddsA gene was amplified by PCR from *P. zeaxanthinifaciens* strain R114 using the primers ddsA/NdeI/for (SEQ ID NO: 9) and ddsA/BamHI/rev (SEQ ID NO: 10). Primer ddsA/Nde/for contains an NdeI (CATATG) restriction site, which is positioned such that the second half coincides with the ATG start codon of the ddsA gene. Primer ddsA/BamHI/rev contains a BamHI site immediately after the stop codon. The PCR fragment was cut with NdeI and BamHI and ligated with the NdeI-BamHI cut backbone of the vector pXI12 (Hümbelin et al., J. Ind. Microbiol. Biotechnol. 22:1-7, 1999), resulting in plasmid pTH36. Next, the vector pBBR1MCS-2 (GenBank accession #U23751) was cut with BstXI and Bsu36I and the larger fragment was ligated with the annealed oligonucleotides MCS-2 up (SEQ ID NO: 11) and MCS-2 down (SEQ ID NO: 12), resulting in vector pBBR-K-Nde. An EcoRI-NdeI-cut fragment with the sequence of SEQ ID NO: 13, containing the rrnB promoter of the ribosomal RNA operon from *Rhodobacter sphaeroides*, was inserted into the EcoRI-NdeI-cut backbone of pBBR-K-Nde, yielding plasmid pBBR-K-PrrnB. Finally, the ddsA gene from strain R114 was excised from pTH36 with NdeI and BamHI and ligated with the NdeI-BamHI cut backbone of vector pBBR-K-PrrnB, resulting in plasmid pBBR-K-PrrnB-ddsA$_{R114}$.

To create a vector for overexpression of the wild-type ddsA gene from *P. zeaxanthinifaciens* ATCC 21588 in *P. zeaxanthinifaciens*, the plasmid pBBR-K-PrrnB-ddsA$_{R114}$ was mutagenized using the QuikChange™ site directed mutagenesis kit (Stratagene) and the primers dds-wt-1 (SEQ ID NO: 14) and dds-wt-2 (SEQ ID NO: 15). The ddsA gene of the resulting plasmid, designated pBBR-K-PrrnB-ddsA$_{wt}$, was completely sequenced and the desired change was verified. The full nucleotide sequence of the ddsA gene from *P. zeaxanthinifaciens* strain ATCC 21588 is shown in SEQ ID NO: 16, and the corresponding amino add sequence is shown in SEQ ID NO: 17. Preliminary experiments to evaluate Coenzyme Q-10 production in recombinant *P. zeaxanthinifaciens* strains indicated that the rrnB promoter used in plasmids pBBR-K-PrrnB-ddsA$_{R114}$ and pBBR-K-PrrnB-ddsA$_{wt}$ caused inconsistency in the results.

Therefore, the rrnB promoter was replaced by the DNA sequence that is located upstream of the crtE gene in the *P. zeaxanthinifaciens* chromosome. This sequence contains the crtE promoter. Plasmids pBBR-K-PcrtE-ddsA$_{wt}$ and pBBR-K-PcrtE-ddsA$_{R114}$ were thus obtained, which carry the EcoRI-NdeI fragment with the sequence of SEQ ID NO: 18 (instead of SEQ ID NO: 13) upstream of the ddsA genes.

Coenzyme Q-10 production in *P. zeaxanthinifaciens* strains overexpressing the ddsA genes. Plasmids pBBR-K-PcrtE-ddsA$_{wt}$ and pBBR-K-PcrtE-ddsA$_{R114}$ were introduced into *P. zeaxanthinifaciens* strains R114, UV9-4, EMS9-7 and R1534intE by electroporation. The resulting recombinant strains and the respective parental (control) strains were grown (in duplicate) in shake flask cultures (medium 362F/2), and production of Coenzyme Q-10 was measured. Initial results indicated that the wild type ddsA gene of *P. zeaxanthinifaciens* ATCC 21588 (SEQ ID NO: 16) codes for a DPP synthase with higher activity than does the mutant ddsA gene from *P. zeaxanthinifaciens* strain R114. Therefore, only the strains overexpressing the wild type ddsA gene were studied further. The data in Table 1 clearly show that increasing the expression of the wild type ddsA gene (via cloning on a multicopy plasmid) significantly increased production of Coenzyme Q-10 in all strains of *P. zeaxanthinifaciens*. The increase in specific production of Coenzyme Q-10 ranged from 2-fold to 8-fold in the different strains tested.

TABLE 1

| | Coenzyme Q-10 | | | | | |
| --- | --- | --- | --- | --- | --- | --- |
| | mg/l (Standard deviation) | | | Specific Formation (mg/g cell dry mass) | | |
| Strain/plasmid | 24 h | 48 h | 72 h | 24 h | 48 h | 72 h |
| R114/pBBR-K (empty vector) | 3.95 (0.71) | 3.9 (0.85) | 4.65 (0.78) | 0.21 | 0.19 | 0.26 |
| R114/pBBR-K-PcrtE-ddsA$_{WT}$ | 19.45 (3.04) | 31.95 (0.64) | 40.3 (1.41) | 0.98 | 1.27 | 2.05 |
| UV9-4 | 4.1 (0.42) | 3.25 (0.21) | 3.2 (0.14) | 0.21 | 0.17 | 0.20 |
| UV9-4/pBBR-K-PcrtE-ddsA$_{WT}$ | 25.05 (0.64) | 25.6 (0.42) | 24.2 (4.38) | 0.89 | 1.22 | 1.21 |
| EMS9-7 | nd | nd | nd | | | |
| EMS9-7/pBBR-K-PcrtE-ddsA$_{WT}$ | 18.1 (2.26) | 24.2 (0.93) | 28.71 (1.40) | 0.85 | 1.27 | 1.58 |
| R1534intE | 13.81 (1.17) | 18.43 (1.63) | 24.26 (3.19) | 0.33 | 0.58 | 1.12 |
| R1534intE/pBBR-K-PcrtE-ddsA$_{WT}$ | 19.64 (3.97) | 34.6 (0.23) | 38.28 (0.93) | 0.94 | 1.61 | 2.27 | nd: not detected

EXAMPLE 5

Cloning and Sequencing of the ubiA Genes from *P. zeaxanthinifaciens* Strains R114 and ATCC 21588

The ubiA gene (coding for 4-hydroxybenzoate polyprenyltransferase) of *P. zeaxanthinifaciens* strain R114 was identified by comparison of the *P. zeaxanthinifaciens* strain R114 genomic sequence with known bacterial 4-hydroxybenzoate polyprenyltransferase sequences. The nucleotide sequence of the ubiA gene of *P. zeaxanthinifaciens* strain R114 (SEQ ID NO: 19) was used to design the forward primer ubiA-Nde (SEQ ID NO: 21) and the reverse primer ubiA-Bam (SEQ ID NO: 22). Primer ubiA-Nde contains an NdeI (CATATG) restriction site, which is positioned such that the second half coincides with the ATG start codon of the ubiA gene. Primer ubiA-BamHI contains a BamHI site immediately after the stop codon. Both primers were used to amplify the ubiA gene using genomic DNA from either *P. zeaxanthinifaciens* strain R114 or *P. zeaxanthinifaciens* ATCC 21588 as template (methods for isolation of genomic DNA, PCR and DNA sequencing are described in Example 3). Both PCR fragments were cloned into vector pCR2.1-TOPO using the TOPO TA Cloning Kit (Invitrogen, Carlsbad, Calif., USA), yielding plasmids pCR2.1-TOPO-ubiA$_{wt}$ (contains the ubiA gene from wild type strain ATCC 21588) and pCR2.1-TOPO-ubiA$_{R114}$ (contains the ubiA gene from mutant strain R114). The cloned insert of each plasmid was sequenced. Comparison of the nucleotide sequence of the ubiA gene from strain ATCC 21588 (SEQ ID NO: 23) with the nucleotide sequence of the ubiA gene from strain R114 (SEQ ID NO: 19) revealed one nucleotide difference that changes codon 220. This difference was confirmed by sequencing the relevant region from uncloned PCR fragments amplified from the genomic DNAs from both strains, to exclude the possibility of a PCR artifact. In the wild type ubiA gene from strain ATCC 21588, codon 220 is ACC (coding for threonine), while in the mutant ubiA gene from strain R114, codon 220 is ATC (coding for isoleucine). The corresponding amino acid sequences of the 4-hydroxybenzoate polyprenyltransferases from *P. zeaxanthinifaciens* strains R114 and ATCC 21588 are given as SEQ ID NO: 20 and SEQ ID NO: 24, respectively.

EXAMPLE 6

Effect of Overexpression of the *P. zeaxanthinifaciens* ubiA Genes on Coenzyme Q-10 Production in *P. zeaxanthinifaciens*

Cloning of the ubiA genes from *P. zeaxanthinifaciens* for overexpression in *P. zeaxanthinifaciens*. The ubiA genes from *P. zeaxanthinifaciens* strains ATCC 21588 and R114 were excised with the restriction endonucleases NdeI and BamHI from the plasmids pCR2.1-TOPO-ubiA$_{wt}$ and pCR2.1-TOPO-ubiA$_{R114}$, respectively (see Example 5) and ligated with the NdeI and BamHI cut vector backbone from the expression plasmid pBBR-K-PcrtE. This placed the ubiA genes under control of the crtE promoter and created plasmids analogous to the expression plasmids pBBR-K-PcrtE-ddsA$_{wt}$ and pBBR-K-PcrtE-ddsA$_{R114}$ described in Example 4. The new plasmids, pBBR-K-PcrtE-ubiA$_{wt}$ and pBBR-K-PcrtE-ubiA$_{R114}$, were used to transform *P. zeaxanthinifaciens* strain R1534 by electroporation. Strain R1534 was selected because it contains a wild-type chromosomal version of the ddsA gene.

Coenzyme Q-10 production in *P. zeaxanthinifaciens* strain R1534 overexpressing the ubiA genes. *P. zeaxanthinifaciens* strains R1534 (control strain), R1534/pBBR-K-PcrtE-ubiA$_{wt}$ and R1534/pBBR-K-PcrtE-ubiA$_{R114}$ were cultivated in bioreactors (in duplicate, conditions described in Example 1) to compare Coenzyme Q-10 production. The results in Table 2 show that overexpression of the ubiA gene from either *P. zeaxanthinifaciens* R114 or ATCC 21588 increased Coenzyme Q-10 production in *P. zeaxanthinifaciens*.

TABLE 2

| | Coenzyme Q-10 | | | |
|---|---|---|---|---|
| | mg/l (Standard deviation) | | Specific formation (mg/g cell dry mass) | |
| | 43 h | 70 h | 43 h | 70 h |
| R1534 | 58.8 (0.54) | 65.8 (0.19) | 1.61 (0.09) | 1.79 (0.01) |
| R1534/pBBR-K-PcrtE-ubiA$_{WT}$ | 63.8 (4.74) | 72.8 (0.62) | 1.77 (0.11) | 2.07 (0.08) |
| R1534/pBBR-K-PcrtE-ubiA$_{R114}$ | 65.5 (0.47) | 85.3 (4.55) | 1.73 (0.01) | 2.14 (0.16) |

---

The invention claimed is:

1. An isolated DNA comprising
   (1) a nucleotide sequence that encodes decaprenyl diphosphate (DPP) synthase, said nucleotide sequence being selected from the group consisting of
      (a) the DNA sequence of SEQ ID NO: 16;
      (b) a DNA sequence which hybridizes under stringent conditions comprising hybridization in a buffer of 40% formamide, 1 M NaCl, 1% sodium dodecyl sulfate (SDS) at 37° C. and at least one wash in 0.2×SSC at a temperature of 60° C. for 20 minutes, to the full length complementary strand of SEQ ID NO: 16, and encodes a polypeptide having the activity of DPP synthase; and
      (c) a DNA sequence which is at least 90% identical to a DNA which codes for the polypeptide of SEQ ID NO: 17, said polypeptide having DPP synthase activity; or
   (2) a nucleotide sequence that encodes 4-hydroxybenzoate polyprenyltransferase, said nucleotide sequence being selected from the group consisting of:
      (a') the DNA sequence of SEQ ID NO: 23;
      (b') a DNA sequence which hybridizes under stringent conditions comprising hybridization in a buffer of 40% formamide, 1 M NaCl, 1% sodium dodecyl sulfate (SDS) at 37° C. and at least one wash in 0.2×SSC at a temperature of 60° C. for 20 minutes, to the full length complementary strand of SEQ ID NO: 23, and encodes a polypeptide having the activity of 4-hydroxybenzoate polyprenyltransferase; and
      (c') a DNA sequence which is at least 90% identical to a DNA which codes for the polypeptide of SEQ ID NO: 24, said polypeptide having 4-hydroxybenzoate polyprenyltransferase activity.

2. A purified polypeptide comprising a polypeptide encoded by a polynucleotide sequence according to claim 1.

3. A construct comprising the DNA according to claim 1.

4. The construct of claim 3 further comprising regulatory sequences.

5. A microorganism transformed with DNA of claim 1.

6. A microorganism comprising a construct according to claim 3 or 4.

7. An isolated polynucleotide comprising the nucleotide sequence of SEQ ID NO: 16.

8. An isolated polynucleotide consisting of the nucleotide sequence of SEQ ID NO: 16.

9. An isolated polynucleotide that encodes the polypeptide sequence of SEQ ID NO: 17.

10. An isolated polynucleotide comprising the nucleotide sequence of SEQ ID NO: 23.

11. An isolated polynucleotide consisting of the nucleotide sequence of SEQ ID NO: 23.

12. An isolated polynucleotide that encodes the polypeptide of SEQ ID NO: 24.

* * * * *

SEQUENCE LISTING

<160> NUMBER OF SEQ ID NOS: 24

<210> SEQ ID NO 1
<211> LENGTH: 30
<212> TYPE: DNA
<213> ORGANISM: Artificial
<220> FEATURE:
<221> NAME/KEY: misc_feature
<222> LOCATION: (1)..(30)
<223> OTHER INFORMATION: forward PCR primer

<400> SEQUENCE: 1
aactgcagtg gccacgtcgc ccatctgtcc        30

<210> SEQ ID NO 2
<211> LENGTH: 33
<212> TYPE: DNA
<213> ORGANISM: Artificial
<220> FEATURE:
<221> NAME/KEY: misc_feature
<222> LOCATION: (1)..(33)
<223> OTHER INFORMATION: reverse PCR primer

<400> SEQUENCE: 2
aactgcagtg gccatcagcc cgccacccat gtc        33

<210> SEQ ID NO 3
<211> LENGTH: 19
<212> TYPE: DNA
<213> ORGANISM: Artificial
<220> FEATURE:
<221> NAME/KEY: misc_feature
<222> LOCATION: (1)..(19)
<223> OTHER INFORMATION: forward PCR primer pCrtEampF

<400> SEQUENCE: 3

```
tgatcttcga cgacatgcc                                                 19
```

<210> SEQ ID NO 4
<211> LENGTH: 21
<212> TYPE: DNA
<213> ORGANISM: Artificial
<220> FEATURE:
<221> NAME/KEY: misc_feature
<222> LOCATION: (1)..(21)
<223> OTHER INFORMATION: reverse PCR primer pCrtEampR

<400> SEQUENCE: 4

```
catccatagt tgcctgactc c                                              21
```

<210> SEQ ID NO 5
<211> LENGTH: 1002
<212> TYPE: DNA
<213> ORGANISM: Paracoccus zeaxanthinifaciens
<220> FEATURE:
<221> NAME/KEY: CDS
<222> LOCATION: (1)..(1002)
<223> OTHER INFORMATION: ddsA gene of Paracoccus zeaxanthinifaciens
      strain R114

<400> SEQUENCE: 5

| atg | aac | gtg | cag | gaa | gac | gtc | cgc | aaa | cca | ctg | gac | cgg | ctg | gcc | gag | 48 |
|---|---|---|---|---|---|---|---|---|---|---|---|---|---|---|---|---|
| Met | Asn | Val | Gln | Glu | Asp | Val | Arg | Lys | Pro | Leu | Asp | Arg | Leu | Ala | Glu | |
| 1 | | | | 5 | | | | | 10 | | | | | 15 | | |

| gcg | ctg | gca | ccc | gag | atg | gag | gcc | gtg | aac | gcg | ctg | atc | cgc | gaa | cgc | 96 |
|---|---|---|---|---|---|---|---|---|---|---|---|---|---|---|---|---|
| Ala | Leu | Ala | Pro | Glu | Met | Glu | Ala | Val | Asn | Ala | Leu | Ile | Arg | Glu | Arg | |
| | | | 20 | | | | | 25 | | | | | 30 | | | |

| atg | gcc | agc | agg | cat | gcg | ccg | cgc | atc | ccc | gag | gtg | acc | gcc | cac | ctg | 144 |
|---|---|---|---|---|---|---|---|---|---|---|---|---|---|---|---|---|
| Met | Ala | Ser | Arg | His | Ala | Pro | Arg | Ile | Pro | Glu | Val | Thr | Ala | His | Leu | |
| | | 35 | | | | | 40 | | | | | 45 | | | | |

| atc | gag | gcc | ggc | ggc | aag | cgc | ctg | cgc | ccg | atg | ctg | acc | ctg | gcc | gcg | 192 |
|---|---|---|---|---|---|---|---|---|---|---|---|---|---|---|---|---|
| Ile | Glu | Ala | Gly | Gly | Lys | Arg | Leu | Arg | Pro | Met | Leu | Thr | Leu | Ala | Ala | |
| 50 | | | | | 55 | | | | | 60 | | | | | | |

| gcg | aag | ctg | ctt | ggc | tat | ggc | ggc | ccc | tat | cac | gtg | cat | ctg | gcc | gcg | 240 |
|---|---|---|---|---|---|---|---|---|---|---|---|---|---|---|---|---|
| Ala | Lys | Leu | Leu | Gly | Tyr | Gly | Gly | Pro | Tyr | His | Val | His | Leu | Ala | Ala | |
| 65 | | | | | 70 | | | | | 75 | | | | | 80 | |

| acg | gtc | gaa | ttc | atc | cac | acc | gcg | acc | ctg | ctg | cat | gac | gac | gtg | gtc | 288 |
|---|---|---|---|---|---|---|---|---|---|---|---|---|---|---|---|---|
| Thr | Val | Glu | Phe | Ile | His | Thr | Ala | Thr | Leu | Leu | His | Asp | Asp | Val | Val | |
| | | | | 85 | | | | | 90 | | | | | 95 | | |

| gac | gaa | agc | cgc | cag | cgc | cgc | ggg | cgt | ccg | acg | gcg | aac | ctg | ctg | tgg | 336 |
|---|---|---|---|---|---|---|---|---|---|---|---|---|---|---|---|---|
| Asp | Glu | Ser | Arg | Gln | Arg | Arg | Gly | Arg | Pro | Thr | Ala | Asn | Leu | Leu | Trp | |
| | | | 100 | | | | | 105 | | | | | 110 | | | |

| gac | aac | aag | tcc | agc | gtg | ctg | gtc | ggc | gat | tac | ctg | ttc | gcg | cgc | agc | 384 |
|---|---|---|---|---|---|---|---|---|---|---|---|---|---|---|---|---|
| Asp | Asn | Lys | Ser | Ser | Val | Leu | Val | Gly | Asp | Tyr | Leu | Phe | Ala | Arg | Ser | |
| | | 115 | | | | | 120 | | | | | 125 | | | | |

| ttc | cag | ctg | atg | gtc | gaa | ccc | ggc | agc | atg | cgc | acg | ctc | gag | atc | ctg | 432 |
|---|---|---|---|---|---|---|---|---|---|---|---|---|---|---|---|---|
| Phe | Gln | Leu | Met | Val | Glu | Pro | Gly | Ser | Met | Arg | Thr | Leu | Glu | Ile | Leu | |
| | 130 | | | | | 135 | | | | | 140 | | | | | |

| tcg | aac | gcc | gcc | gcc | acc | atc | gcc | gag | ggc | gag | gtg | ctg | cag | ctg | acc | 480 |
|---|---|---|---|---|---|---|---|---|---|---|---|---|---|---|---|---|
| Ser | Asn | Ala | Ala | Ala | Thr | Ile | Ala | Glu | Gly | Glu | Val | Leu | Gln | Leu | Thr | |
| 145 | | | | | 150 | | | | | 155 | | | | | 160 | |

| gcg | gcg | cag | gat | ctg | gcc | acg | aac | gag | gac | atc | tat | ctg | cag | gtc | gtg | 528 |
|---|---|---|---|---|---|---|---|---|---|---|---|---|---|---|---|---|
| Ala | Ala | Gln | Asp | Leu | Ala | Thr | Asn | Glu | Asp | Ile | Tyr | Leu | Gln | Val | Val | |
| | | | | 165 | | | | | 170 | | | | | 175 | | |

| cgc | ggc | aag | acg | gca | gcg | ctg | ttc | tcg | gcc | gcg | acc | gag | gtg | ggc | ggc | 576 |
|---|---|---|---|---|---|---|---|---|---|---|---|---|---|---|---|---|
| Arg | Gly | Lys | Thr | Ala | Ala | Leu | Phe | Ser | Ala | Ala | Thr | Glu | Val | Gly | Gly | |
| | | | 180 | | | | | 185 | | | | | 190 | | | |

| gtc | atc | gcg | ggc | gtc | ccc | gat | gcg | cag | gtc | cgc | gcg | ctg | ttc | gat | tac | 624 |

```
                                                                                  -continued Val Ile Ala Gly Val Pro Asp Ala Gln Val Arg Ala Leu Phe Asp Tyr
        195                 200                 205 ggc gac gcg ctt ggc atc gcc ttc cag atc gtg gac gac ctg ctg gat           672
Gly Asp Ala Leu Gly Ile Ala Phe Gln Ile Val Asp Asp Leu Leu Asp
210                 215                 220 tac ggc ggc acc gcc gag gcg atc gac aag aat acc ggc gac gat ttc           720
Tyr Gly Gly Thr Ala Glu Ala Ile Asp Lys Asn Thr Gly Asp Asp Phe
225                 230                 235                 240 cgc gaa cgc aag ctg acg ctg ccg gtg atc aag gcc gtg gcc cgc gcc           768
Arg Glu Arg Lys Leu Thr Leu Pro Val Ile Lys Ala Val Ala Arg Ala
            245                 250                 255 acc ccc gag gaa cgc gcc ttc tgg tcg cgc acc atc gag aag ggc gac           816
Thr Pro Glu Glu Arg Ala Phe Trp Ser Arg Thr Ile Glu Lys Gly Asp
        260                 265                 270 cag aag gac ggc gac ctt gaa cac gcg ctg gaa ctg ctg gcc cgc cac           864
Gln Lys Asp Gly Asp Leu Glu His Ala Leu Glu Leu Leu Ala Arg His
    275                 280                 285 ggc gcg atg gcc gat gcc cgc cgc gac gcg ctg gac tgg gcg gcc agg           912
Gly Ala Met Ala Asp Ala Arg Arg Asp Ala Leu Asp Trp Ala Ala Arg
290                 295                 300 gcc cgc gcc tcc ctg cag atc ctg ccc gag cat ccg atc cgc gac atg           960
Ala Arg Ala Ser Leu Gln Ile Leu Pro Glu His Pro Ile Arg Asp Met
305                 310                 315                 320 ctg tcg gac ctg gcc gat ttc gtg gtc gaa cgc atc gcc tga               1002
Leu Ser Asp Leu Ala Asp Phe Val Val Glu Arg Ile Ala
            325                 330

<210> SEQ ID NO 6
<211> LENGTH: 333
<212> TYPE: PRT
<213> ORGANISM: Paracoccus zeaxanthinifaciens

<400> SEQUENCE: 6

Met Asn Val Gln Glu Asp Val Arg Lys Pro Leu Asp Arg Leu Ala Glu
1               5                  10                  15

Ala Leu Ala Pro Glu Met Glu Ala Val Asn Ala Leu Ile Arg Glu Arg
            20                  25                  30

Met Ala Ser Arg His Ala Pro Arg Ile Pro Glu Val Thr Ala His Leu
        35                  40                  45

Ile Glu Ala Gly Gly Lys Arg Leu Arg Pro Met Leu Thr Leu Ala Ala
    50                  55                  60

Ala Lys Leu Leu Gly Tyr Gly Gly Pro Tyr His Val His Leu Ala Ala
65                  70                  75                  80

Thr Val Glu Phe Ile His Thr Ala Thr Leu Leu His Asp Asp Val Val
                85                  90                  95

Asp Glu Ser Arg Gln Arg Arg Gly Arg Pro Thr Ala Asn Leu Leu Trp
            100                 105                 110

Asp Asn Lys Ser Ser Val Leu Val Gly Asp Tyr Leu Phe Ala Arg Ser
        115                 120                 125

Phe Gln Leu Met Val Glu Pro Gly Ser Met Arg Thr Leu Glu Ile Leu
    130                 135                 140

Ser Asn Ala Ala Ala Thr Ile Ala Glu Gly Glu Val Leu Gln Leu Thr
145                 150                 155                 160

Ala Ala Gln Asp Leu Ala Thr Asn Glu Asp Ile Tyr Leu Gln Val Val
                165                 170                 175

Arg Gly Lys Thr Ala Ala Leu Phe Ser Ala Ala Thr Glu Val Gly Gly
            180                 185                 190
```

Val Ile Ala Gly Val Pro Asp Ala Gln Val Arg Ala Leu Phe Asp Tyr
        195                 200                 205

Gly Asp Ala Leu Gly Ile Ala Phe Gln Ile Val Asp Leu Leu Asp
210                 215                 220

Tyr Gly Gly Thr Ala Glu Ala Ile Asp Lys Asn Thr Gly Asp Asp Phe
225                 230                 235                 240

Arg Glu Arg Lys Leu Thr Leu Pro Val Ile Lys Ala Val Ala Arg Ala
                245                 250                 255

Thr Pro Glu Glu Arg Ala Phe Trp Ser Arg Thr Ile Glu Lys Gly Asp
                260                 265                 270

Gln Lys Asp Gly Asp Leu Glu His Ala Leu Glu Leu Leu Ala Arg His
                275                 280                 285

Gly Ala Met Ala Asp Ala Arg Arg Asp Ala Leu Asp Trp Ala Ala Arg
290                 295                 300

Ala Arg Ala Ser Leu Gln Ile Leu Pro Glu His Pro Ile Arg Asp Met
305                 310                 315                 320

Leu Ser Asp Leu Ala Asp Phe Val Val Glu Arg Ile Ala
                325                 330

<210> SEQ ID NO 7
<211> LENGTH: 20
<212> TYPE: DNA
<213> ORGANISM: Artificial
<220> FEATURE:
<221> NAME/KEY: misc_feature
<222> LOCATION: (1)..(20)
<223> OTHER INFORMATION: forward PCR primer 7R-01

<400> SEQUENCE: 7
ttcatgatga cgtggtcgaa                                              20

<210> SEQ ID NO 8
<211> LENGTH: 20
<212> TYPE: DNA
<213> ORGANISM: Artificial
<220> FEATURE:
<221> NAME/KEY: misc_feature
<222> LOCATION: (1)..(20)
<223> OTHER INFORMATION: reverse PCR primer dds-3

<400> SEQUENCE: 8
gcgcaatgcg gcccgcccct                                              20

<210> SEQ ID NO 9
<211> LENGTH: 31
<212> TYPE: DNA
<213> ORGANISM: Artificial
<220> FEATURE:
<221> NAME/KEY: misc_feature
<222> LOCATION: (1)..(31)
<223> OTHER INFORMATION: PCR primer ddsA/NdeI/for

<400> SEQUENCE: 9
atgccatatg aacgtgcagg aagacgtccg c                                 31

<210> SEQ ID NO 10
<211> LENGTH: 35
<212> TYPE: DNA
<213> ORGANISM: Artificial
<220> FEATURE:
<221> NAME/KEY: misc_feature
<222> LOCATION: (1)..(35)
<223> OTHER INFORMATION: PCR primer ddsA/BamHI/rev

```
<400> SEQUENCE: 10
gcatggatcc ttatcaggcg atgcgttcga ccacg                              35

<210> SEQ ID NO 11
<211> LENGTH: 36
<212> TYPE: DNA
<213> ORGANISM: Artificial
<220> FEATURE:
<221> NAME/KEY: misc_feature
<222> LOCATION: (1)..(36)
<223> OTHER INFORMATION: synthetic DNA MCS-2 up

<400> SEQUENCE: 11
tcagaattcg gtaccatatg aagcttggat ccgggg                             36

<210> SEQ ID NO 12
<211> LENGTH: 29
<212> TYPE: DNA
<213> ORGANISM: Artificial
<220> FEATURE:
<221> NAME/KEY: misc_feature
<222> LOCATION: (1)..(29)
<223> OTHER INFORMATION: synthetic DNA MCS-2 down

<400> SEQUENCE: 12
ggatccaagc ttcatatggt accgaattc                                    29

<210> SEQ ID NO 13
<211> LENGTH: 342
<212> TYPE: DNA
<213> ORGANISM: Rhodobacter sphaeroides

<400> SEQUENCE: 13
gaattcctgc aggtcgtctc gcgcaccctc tgcggcggcc ggacgactac cggaggctct    60
gagtcgccgc gcaggtcggg cgaaaggggc gggtcgcggc tccgcggcaa cgaaaaacgc   120
caagatttct tggctgcgac atgaaatgtt acggagccca aaaaatccgc ttgcgcccgg   180
ggccgtctgc tcctagaacc gcttcaccga gacgaagacc ggcagcgccg acgagacg     240 agggagggat gacagaaacg tcggccgcga caattgaaga tgaggcggac gggatgctgg   300
ttgtctgtcg actctagacg atcgcctacc ggagtacata tg                      342

<210> SEQ ID NO 14
<211> LENGTH: 31
<212> TYPE: DNA
<213> ORGANISM: Artificial
<220> FEATURE:
<221> NAME/KEY: misc_feature
<222> LOCATION: (1)..(31)
<223> OTHER INFORMATION: PCR primer dds-wt-1

<400> SEQUENCE: 14
ccgccgaggc gatcggcaag aataccggcg a                                  31

<210> SEQ ID NO 15
<211> LENGTH: 31
<212> TYPE: DNA
<213> ORGANISM: Artificial
<220> FEATURE:
<221> NAME/KEY: misc_feature
<222> LOCATION: (1)..(31)
<223> OTHER INFORMATION: PCR primer dds-wt-2

<400> SEQUENCE: 15
tcgccggtat tcttgccgat cgcctcggcg g                                  31
```

<210> SEQ ID NO 16
<211> LENGTH: 1002
<212> TYPE: DNA
<213> ORGANISM: Paracoccus zeaxanthinifaciens
<220> FEATURE:
<221> NAME/KEY: CDS
<222> LOCATION: (1)..(1002)
<223> OTHER INFORMATION: ddsA gene of Paracoccus zeaxanthinifaciens strain ATCC 21588

<400> SEQUENCE: 16

| | | | | | | | | | | | | | | | | |
|---|---|---|---|---|---|---|---|---|---|---|---|---|---|---|---|---|
| atg | aac | gtg | cag | gaa | gac | gtc | cgc | aaa | cca | ctg | gac | cgg | ctg | gcc | gag | 48 |
| Met | Asn | Val | Gln | Glu | Asp | Val | Arg | Lys | Pro | Leu | Asp | Arg | Leu | Ala | Glu | |
| 1 | | | | 5 | | | | | 10 | | | | | 15 | | |
| gcg | ctg | gca | ccc | gag | atg | gag | gcc | gtg | aac | gcg | ctg | atc | cgc | gaa | cgc | 96 |
| Ala | Leu | Ala | Pro | Glu | Met | Glu | Ala | Val | Asn | Ala | Leu | Ile | Arg | Glu | Arg | |
| | | | 20 | | | | | 25 | | | | | 30 | | | |
| atg | gcc | agc | agg | cat | gcg | ccg | cgc | atc | ccc | gag | gtg | acc | gcc | cac | ctg | 144 |
| Met | Ala | Ser | Arg | His | Ala | Pro | Arg | Ile | Pro | Glu | Val | Thr | Ala | His | Leu | |
| | | 35 | | | | | 40 | | | | | 45 | | | | |
| atc | gag | gcc | ggc | ggc | aag | cgc | ctg | cgc | ccg | atg | ctg | acc | ctg | gcc | gcg | 192 |
| Ile | Glu | Ala | Gly | Gly | Lys | Arg | Leu | Arg | Pro | Met | Leu | Thr | Leu | Ala | Ala | |
| | 50 | | | | | 55 | | | | | 60 | | | | | |
| gcg | aag | ctg | ctt | ggc | tat | ggc | ggc | ccc | tat | cac | gtg | cat | ctg | gcc | gcg | 240 |
| Ala | Lys | Leu | Leu | Gly | Tyr | Gly | Gly | Pro | Tyr | His | Val | His | Leu | Ala | Ala | |
| 65 | | | | | 70 | | | | | 75 | | | | | 80 | |
| acg | gtc | gaa | ttc | atc | cac | acc | gcg | acc | ctg | ctg | cat | gac | gac | gtg | gtc | 288 |
| Thr | Val | Glu | Phe | Ile | His | Thr | Ala | Thr | Leu | Leu | His | Asp | Asp | Val | Val | |
| | | | | 85 | | | | | 90 | | | | | 95 | | |
| gac | gaa | agc | cgc | cag | cgc | cgc | ggg | cgt | ccg | acg | gcg | aac | ctg | ctg | tgg | 336 |
| Asp | Glu | Ser | Arg | Gln | Arg | Arg | Gly | Arg | Pro | Thr | Ala | Asn | Leu | Leu | Trp | |
| | | | 100 | | | | | 105 | | | | | 110 | | | |
| gac | aac | aag | tcc | agc | gtg | ctg | gtc | ggc | gat | tac | ctg | ttc | gcg | cgc | agc | 384 |
| Asp | Asn | Lys | Ser | Ser | Val | Leu | Val | Gly | Asp | Tyr | Leu | Phe | Ala | Arg | Ser | |
| | | 115 | | | | | 120 | | | | | 125 | | | | |
| ttc | cag | ctg | atg | gtc | gaa | ccc | ggc | agc | atg | cgc | acg | ctc | gag | atc | ctg | 432 |
| Phe | Gln | Leu | Met | Val | Glu | Pro | Gly | Ser | Met | Arg | Thr | Leu | Glu | Ile | Leu | |
| | 130 | | | | | 135 | | | | | 140 | | | | | |
| tcg | aac | gcc | gcc | gcc | acc | atc | gcc | gag | ggc | gag | gtg | ctg | cag | ctg | acc | 480 |
| Ser | Asn | Ala | Ala | Ala | Thr | Ile | Ala | Glu | Gly | Glu | Val | Leu | Gln | Leu | Thr | |
| 145 | | | | | 150 | | | | | 155 | | | | | 160 | |
| gcg | gcg | cag | gat | ctg | gcc | acg | aac | gag | gac | atc | tat | ctg | cag | gtc | gtg | 528 |
| Ala | Ala | Gln | Asp | Leu | Ala | Thr | Asn | Glu | Asp | Ile | Tyr | Leu | Gln | Val | Val | |
| | | | | 165 | | | | | 170 | | | | | 175 | | |
| cgc | ggc | aag | acg | gca | gcg | ctg | ttc | tcg | gcc | gcg | acc | gag | gtg | ggc | ggc | 576 |
| Arg | Gly | Lys | Thr | Ala | Ala | Leu | Phe | Ser | Ala | Ala | Thr | Glu | Val | Gly | Gly | |
| | | | 180 | | | | | 185 | | | | | 190 | | | |
| gtc | atc | gcg | ggc | gtc | ccc | gat | gcg | cag | gtc | cgc | gcg | ctg | ttc | gat | tac | 624 |
| Val | Ile | Ala | Gly | Val | Pro | Asp | Ala | Gln | Val | Arg | Ala | Leu | Phe | Asp | Tyr | |
| | | 195 | | | | | 200 | | | | | 205 | | | | |
| ggc | gac | gcg | ctt | ggc | atc | gcc | ttc | cag | atc | gtg | gac | gac | ctg | ctg | gat | 672 |
| Gly | Asp | Ala | Leu | Gly | Ile | Ala | Phe | Gln | Ile | Val | Asp | Asp | Leu | Leu | Asp | |
| | 210 | | | | | 215 | | | | | 220 | | | | | |
| tac | ggc | ggc | acc | gcc | gag | gcg | atc | ggc | aag | aat | acc | ggc | gac | gat | ttc | 720 |
| Tyr | Gly | Gly | Thr | Ala | Glu | Ala | Ile | Gly | Lys | Asn | Thr | Gly | Asp | Asp | Phe | |
| 225 | | | | | 230 | | | | | 235 | | | | | 240 | |
| cgc | gaa | cgc | aag | ctg | acg | ctg | ccg | gtg | atc | aag | gcc | gtg | gcc | cgc | gcc | 768 |
| Arg | Glu | Arg | Lys | Leu | Thr | Leu | Pro | Val | Ile | Lys | Ala | Val | Ala | Arg | Ala | |
| | | | | 245 | | | | | 250 | | | | | 255 | | |
| acc | ccc | gag | gaa | cgc | gcc | ttc | tgg | tcg | cgc | acc | atc | gag | aag | ggc | gac | 816 |

```
Thr Pro Glu Glu Arg Ala Phe Trp Ser Arg Thr Ile Glu Lys Gly Asp
            260                 265                 270 cag aag gac ggc gac ctt gaa cac gcg ctg gaa ctg ctg gcc cgc cac      864
Gln Lys Asp Gly Asp Leu Glu His Ala Leu Glu Leu Leu Ala Arg His
        275                 280                 285 ggc gcg atg gcc gat gcc cgc cgc gac gcg ctg gac tgg gcg gcc agg      912
Gly Ala Met Ala Asp Ala Arg Arg Asp Ala Leu Asp Trp Ala Ala Arg
    290                 295                 300 gcc cgc gcc tcc ctg cag atc ctg ccc gag cat ccg atc cgc gac atg      960
Ala Arg Ala Ser Leu Gln Ile Leu Pro Glu His Pro Ile Arg Asp Met
305                 310                 315                 320 ctg tcg gac ctg gcc gat ttc gtg gtc gaa cgc atc gcc tga             1002
Leu Ser Asp Leu Ala Asp Phe Val Val Glu Arg Ile Ala
                325                 330
```

<210> SEQ ID NO 17
<211> LENGTH: 333
<212> TYPE: PRT
<213> ORGANISM: Paracoccus zeaxanthinifaciens

<400> SEQUENCE: 17

```
Met Asn Val Gln Glu Asp Val Arg Lys Pro Leu Asp Arg Leu Ala Glu
1               5                   10                  15

Ala Leu Ala Pro Glu Met Glu Ala Val Asn Ala Leu Ile Arg Glu Arg
            20                  25                  30

Met Ala Ser Arg His Ala Pro Arg Ile Pro Glu Val Thr Ala His Leu
        35                  40                  45

Ile Glu Ala Gly Gly Lys Arg Leu Arg Pro Met Leu Thr Leu Ala Ala
    50                  55                  60

Ala Lys Leu Leu Gly Tyr Gly Gly Pro Tyr His Val His Leu Ala Ala
65                  70                  75                  80

Thr Val Glu Phe Ile His Thr Ala Thr Leu Leu His Asp Asp Val Val
                85                  90                  95

Asp Glu Ser Arg Gln Arg Arg Gly Arg Pro Thr Ala Asn Leu Leu Trp
            100                 105                 110

Asp Asn Lys Ser Ser Val Leu Val Gly Asp Tyr Leu Phe Ala Arg Ser
        115                 120                 125

Phe Gln Leu Met Val Glu Pro Gly Ser Met Arg Thr Leu Glu Ile Leu
    130                 135                 140

Ser Asn Ala Ala Ala Thr Ile Ala Glu Gly Glu Val Leu Gln Leu Thr
145                 150                 155                 160

Ala Ala Gln Asp Leu Ala Thr Asn Glu Asp Ile Tyr Leu Gln Val Val
                165                 170                 175

Arg Gly Lys Thr Ala Ala Leu Phe Ser Ala Ala Thr Glu Val Gly Gly
            180                 185                 190

Val Ile Ala Gly Val Pro Asp Ala Gln Val Arg Ala Leu Phe Asp Tyr
        195                 200                 205

Gly Asp Ala Leu Gly Ile Ala Phe Gln Ile Val Asp Asp Leu Leu Asp
    210                 215                 220

Tyr Gly Gly Thr Ala Glu Ala Ile Gly Lys Asn Thr Gly Asp Asp Phe
225                 230                 235                 240

Arg Glu Arg Lys Leu Thr Leu Pro Val Ile Lys Ala Val Ala Arg Ala
                245                 250                 255

Thr Pro Glu Glu Arg Ala Phe Trp Ser Arg Thr Ile Glu Lys Gly Asp
            260                 265                 270

Gln Lys Asp Gly Asp Leu Glu His Ala Leu Glu Leu Leu Ala Arg His
        275
```

```
                275                 280                 285
Gly Ala Met Ala Asp Ala Arg Arg Asp Ala Leu Asp Trp Ala Ala Arg
        290                 295                 300

Ala Arg Ala Ser Leu Gln Ile Leu Pro Glu His Pro Ile Arg Asp Met
305                 310                 315                 320

Leu Ser Asp Leu Ala Asp Phe Val Val Glu Arg Ile Ala
                325                 330

<210> SEQ ID NO 18
<211> LENGTH: 277
<212> TYPE: DNA
<213> ORGANISM: Artificial
<220> FEATURE:
<221> NAME/KEY: misc_feature
<222> LOCATION: (1)..(277)
<223> OTHER INFORMATION: EcoRI-NdeI fragment containing PcrtE promoter

<400> SEQUENCE: 18
gaattcgctg ctgaacgcga tggcggcgcg gggcgcgacg cgcggggccg catccgtctg      60
catcggcggg ggcgaggcga cggccatcgc gctggaacgg ctgagctaat tcatttgcgc     120
gaatccgcgt ttttcgtgca cgatggggga accggaaacg gccacgcctg ttgtggttgc     180
gtcgacctgt cttcgggcca tgcccgtgac gcgatgtggc aggcgcatgg ggcgttgccg     240
atccggtcgc atgactgacg caacgaaggc acatatg                              277

<210> SEQ ID NO 19
<211> LENGTH: 975
<212> TYPE: DNA
<213> ORGANISM: Paracoccus zeaxanthinifaciens
<220> FEATURE:
<221> NAME/KEY: CDS
<222> LOCATION: (1)..(975)
<223> OTHER INFORMATION: ubiA gene of Paracoccus zeaxanthinifaciens
      strain R114

<400> SEQUENCE: 19 atg aac aat cgt atc ttc gcc atg atg ggc aac gct atg caa agc agc       48
Met Asn Asn Arg Ile Phe Ala Met Met Gly Asn Ala Met Gln Ser Ser
1               5                   10                  15 acg gaa aga cca gac gcg gtc gtc gac gcg ccg aag gga aac tgg gtc       96
Thr Glu Arg Pro Asp Ala Val Val Asp Ala Pro Lys Gly Asn Trp Val
                20                  25                  30 gat gag atc gcc ccg cca tgg tcg cgc ccc tgg ctg cgg ctc agc cgc      144
Asp Glu Ile Ala Pro Pro Trp Ser Arg Pro Trp Leu Arg Leu Ser Arg
            35                  40                  45 gcg gac cgg ccc atc ggg aca tgg ctg ctg ctg ccc tgc tgg tgg           192
Ala Asp Arg Pro Ile Gly Thr Trp Leu Leu Leu Pro Cys Trp Trp
        50                  55                  60 ggg atc ggg ctg gcg atg atg gca gac ggg ccg cgc tgg ttc gat gcg      240
Gly Ile Gly Leu Ala Met Met Ala Asp Gly Pro Arg Trp Phe Asp Ala
65                  70                  75                  80 tgg atc gcg ctg gcc tgc acc atc ggc gcc ttc gtc atg cgg ggc gcg      288
Trp Ile Ala Leu Ala Cys Thr Ile Gly Ala Phe Val Met Arg Gly Ala
                85                  90                  95 ggc tgc acc tgg aac gac atc acc gac cgc cgg atc gac gcg cag gtc      336
Gly Cys Thr Trp Asn Asp Ile Thr Asp Arg Arg Ile Asp Ala Gln Val
                100                 105                 110 gca cgc acc cgc tcg cgc ccg ctg cca agc gga cag gtc acg ctg cgg      384
Ala Arg Thr Arg Ser Arg Pro Leu Pro Ser Gly Gln Val Thr Leu Arg
            115                 120                 125 ggc gcc tat ggc tgg ctg atc gcg cag ggg ctg atc ggg ctg gcg atc      432
```

```
              Gly Ala Tyr Gly Trp Leu Ile Ala Gln Gly Leu Ile Gly Leu Ala Ile
                  130                 135                 140 ctg ctg acc ctg ggg cag gcc gcg atc tgg atg ggc gtc gcc tcg ctg          480
Leu Leu Thr Leu Gly Gln Ala Ala Ile Trp Met Gly Val Ala Ser Leu
145                 150                 155                 160 gcg ctg gtc gcg atc tat ccc ttc gcg aaa cgc ttc acc tgg tgg ccg          528
Ala Leu Val Ala Ile Tyr Pro Phe Ala Lys Arg Phe Thr Trp Trp Pro
                165                 170                 175 cag atc ttc ctg ggg ctg gcc ttc aac tgg ggc gtc atg ctg gcc tat          576
Gln Ile Phe Leu Gly Leu Ala Phe Asn Trp Gly Val Met Leu Ala Tyr
            180                 185                 190 gcc gcg cat gcg ggc cgt gtc gat gcg gcc cct gtc gtg gca tgg ctg          624
Ala Ala His Ala Gly Arg Val Asp Ala Ala Pro Val Val Ala Trp Leu
        195                 200                 205 ggg gcc atc gcc tgg acg atc ttc tac gac acc atc tat gcc cac cag          672
Gly Ala Ile Ala Trp Thr Ile Phe Tyr Asp Thr Ile Tyr Ala His Gln
    210                 215                 220 gac gcc gag gac gac gcc ctg atc ggg gtg aaa tcc acc gcg cgg ctg          720
Asp Ala Glu Asp Asp Ala Leu Ile Gly Val Lys Ser Thr Ala Arg Leu
225                 230                 235                 240 ttc ggc gac aaa agc ccg cgc atc ctt gcg gga ttc gcc ctg ggc gcg          768
Phe Gly Asp Lys Ser Pro Arg Ile Leu Ala Gly Phe Ala Leu Gly Ala
                245                 250                 255 gtc ctg gtg ctg atg ctg gcc acc gcg ctg ccc ggt cgc aat ctg ttg          816
Val Leu Val Leu Met Leu Ala Thr Ala Leu Pro Gly Arg Asn Leu Leu
            260                 265                 270 att gcc tgg gcg ggc gtc gcg ggt ttc ggc ctg cac cta ggc tgg cag          864
Ile Ala Trp Ala Gly Val Ala Gly Phe Gly Leu His Leu Gly Trp Gln
        275                 280                 285 ctt cgc aaa ttc cag ccg gat cag ggc gat acc tgc ctg cgc ctg ttc          912
Leu Arg Lys Phe Gln Pro Asp Gln Gly Asp Thr Cys Leu Arg Leu Phe
    290                 295                 300 cgg tcc aac cgc gat gcg ggg ctg atc ctt gcg ctg ttt ctt gcc gtg          960
Arg Ser Asn Arg Asp Ala Gly Leu Ile Leu Ala Leu Phe Leu Ala Val
305                 310                 315                 320 gcg ggc ctc gca tga                                                      975
Ala Gly Leu Ala <210> SEQ ID NO 20
<211> LENGTH: 324
<212> TYPE: PRT
<213> ORGANISM: Paracoccus zeaxanthinifaciens

<400> SEQUENCE: 20

Met Asn Asn Arg Ile Phe Ala Met Met Gly Asn Ala Met Gln Ser Ser
1               5                   10                  15

Thr Glu Arg Pro Asp Ala Val Val Asp Ala Pro Lys Gly Asn Trp Val
                20                  25                  30

Asp Glu Ile Ala Pro Pro Trp Ser Arg Pro Trp Leu Arg Leu Ser Arg
            35                  40                  45

Ala Asp Arg Pro Ile Gly Thr Trp Leu Leu Leu Pro Cys Trp Trp
        50                  55                  60

Gly Ile Gly Leu Ala Met Met Ala Asp Gly Pro Arg Trp Phe Asp Ala
65                  70                  75                  80

Trp Ile Ala Leu Ala Cys Thr Ile Gly Ala Phe Val Met Arg Gly Ala
                85                  90                  95

Gly Cys Thr Trp Asn Asp Ile Thr Asp Arg Arg Ile Asp Ala Gln Val
                100                 105                 110
```

```
Ala Arg Thr Arg Ser Arg Pro Leu Pro Ser Gly Gln Val Thr Leu Arg
        115                 120                 125

Gly Ala Tyr Gly Trp Leu Ile Ala Gln Gly Leu Ile Gly Leu Ala Ile
    130                 135                 140

Leu Leu Thr Leu Gly Gln Ala Ala Ile Trp Met Gly Val Ala Ser Leu
145                 150                 155                 160

Ala Leu Val Ala Ile Tyr Pro Phe Ala Lys Arg Phe Thr Trp Trp Pro
                165                 170                 175

Gln Ile Phe Leu Gly Leu Ala Phe Asn Trp Gly Val Met Leu Ala Tyr
                180                 185                 190

Ala Ala His Ala Gly Arg Val Asp Ala Ala Pro Val Val Ala Trp Leu
            195                 200                 205

Gly Ala Ile Ala Trp Thr Ile Phe Tyr Asp Thr Ile Tyr Ala His Gln
        210                 215                 220

Asp Ala Glu Asp Asp Ala Leu Ile Gly Val Lys Ser Thr Ala Arg Leu
225                 230                 235                 240

Phe Gly Asp Lys Ser Pro Arg Ile Leu Ala Gly Phe Ala Leu Gly Ala
                245                 250                 255

Val Leu Val Leu Met Leu Ala Thr Ala Leu Pro Gly Arg Asn Leu Leu
                260                 265                 270

Ile Ala Trp Ala Gly Val Ala Gly Phe Gly Leu His Leu Gly Trp Gln
            275                 280                 285

Leu Arg Lys Phe Gln Pro Asp Gln Gly Asp Thr Cys Leu Arg Leu Phe
        290                 295                 300

Arg Ser Asn Arg Asp Ala Gly Leu Ile Leu Ala Leu Phe Leu Ala Val
305                 310                 315                 320

Ala Gly Leu Ala

<210> SEQ ID NO 21
<211> LENGTH: 30
<212> TYPE: DNA
<213> ORGANISM: Artificial
<220> FEATURE:
<221> NAME/KEY: misc_feature
<222> LOCATION: (1)..(30)
<223> OTHER INFORMATION: PCR primer ubiA-Nde

<400> SEQUENCE: 21
aaggcctcat atgaacaatc gtatcttcgc                                        30

<210> SEQ ID NO 22
<211> LENGTH: 28
<212> TYPE: DNA
<213> ORGANISM: Artificial
<220> FEATURE:
<221> NAME/KEY: misc_feature
<222> LOCATION: (1)..(28)
<223> OTHER INFORMATION: PCR primer ubiA-Bam

<400> SEQUENCE: 22
cgggatcctc atgcgaggcc cgccacgg                                          28

<210> SEQ ID NO 23
<211> LENGTH: 975
<212> TYPE: DNA
<213> ORGANISM: Paracoccus zeaxanthinifaciens
<220> FEATURE:
<221> NAME/KEY: CDS
<222> LOCATION: (1)..(975)
<223> OTHER INFORMATION: ubiA gene from Paracoccus zeaxanthinifaciens
      strain ATCC 21588
```

-continued

<400> SEQUENCE: 23

| | | | | | | | | | | | | | | | | |
|---|---|---|---|---|---|---|---|---|---|---|---|---|---|---|---|---|
| atg | aac | aat | cgt | atc | ttc | gcc | atg | atg | ggc | aac | gct | atg | caa | agc | agc | 48 |
| Met | Asn | Asn | Arg | Ile | Phe | Ala | Met | Met | Gly | Asn | Ala | Met | Gln | Ser | Ser | |
| 1 | | | | 5 | | | | | 10 | | | | | 15 | | |
| acg | gaa | aga | cca | gac | gcg | gtc | gtc | gac | gcg | ccg | aag | gga | aac | tgg | gtc | 96 |
| Thr | Glu | Arg | Pro | Asp | Ala | Val | Val | Asp | Ala | Pro | Lys | Gly | Asn | Trp | Val | |
| | | | 20 | | | | | 25 | | | | | 30 | | | |
| gat | gag | atc | gcc | ccg | cca | tgg | tcg | cgc | ccc | tgg | ctg | cgg | ctc | agc | cgc | 144 |
| Asp | Glu | Ile | Ala | Pro | Pro | Trp | Ser | Arg | Pro | Trp | Leu | Arg | Leu | Ser | Arg | |
| | | 35 | | | | | 40 | | | | | 45 | | | | |
| gcg | gac | cgg | ccc | atc | ggg | aca | tgg | ctg | ctg | ctg | ccc | tgc | tgg | tgg | | 192 |
| Ala | Asp | Arg | Pro | Ile | Gly | Thr | Trp | Leu | Leu | Leu | Leu | Pro | Cys | Trp | Trp | |
| | 50 | | | | | 55 | | | | | 60 | | | | | |
| ggg | atc | ggg | ctg | gcg | atg | atg | gca | gac | ggg | ccg | cgc | tgg | ttc | gat | gcg | 240 |
| Gly | Ile | Gly | Leu | Ala | Met | Met | Ala | Asp | Gly | Pro | Arg | Trp | Phe | Asp | Ala | |
| 65 | | | | | 70 | | | | | 75 | | | | | 80 | |
| tgg | atc | gcg | ctg | gcc | tgc | acc | atc | ggc | gcc | ttc | gtc | atg | cgg | ggc | gcg | 288 |
| Trp | Ile | Ala | Leu | Ala | Cys | Thr | Ile | Gly | Ala | Phe | Val | Met | Arg | Gly | Ala | |
| | | | | 85 | | | | | 90 | | | | | 95 | | |
| ggc | tgc | acc | tgg | aac | gac | atc | acc | gac | cgc | cgg | atc | gac | gcg | cag | gtc | 336 |
| Gly | Cys | Thr | Trp | Asn | Asp | Ile | Thr | Asp | Arg | Arg | Ile | Asp | Ala | Gln | Val | |
| | | | 100 | | | | | 105 | | | | | 110 | | | |
| gca | cgc | acc | cgc | tcg | cgc | ccg | ctg | cca | agc | gga | cag | gtc | acg | ctg | cgg | 384 |
| Ala | Arg | Thr | Arg | Ser | Arg | Pro | Leu | Pro | Ser | Gly | Gln | Val | Thr | Leu | Arg | |
| | | 115 | | | | | 120 | | | | | 125 | | | | |
| ggc | gcc | tat | ggc | tgg | ctg | atc | gcg | cag | ggg | ctg | atc | ggg | ctg | gcg | atc | 432 |
| Gly | Ala | Tyr | Gly | Trp | Leu | Ile | Ala | Gln | Gly | Leu | Ile | Gly | Leu | Ala | Ile | |
| | 130 | | | | | 135 | | | | | 140 | | | | | |
| ctg | ctg | acc | ctg | ggg | cag | gcc | gcg | atc | tgg | atg | ggc | gtc | gcc | tcg | ctg | 480 |
| Leu | Leu | Thr | Leu | Gly | Gln | Ala | Ala | Ile | Trp | Met | Gly | Val | Ala | Ser | Leu | |
| 145 | | | | | 150 | | | | | 155 | | | | | 160 | |
| gcg | ctg | gtc | gcg | atc | tat | ccc | ttc | gcg | aaa | cgc | ttc | acc | tgg | tgg | ccg | 528 |
| Ala | Leu | Val | Ala | Ile | Tyr | Pro | Phe | Ala | Lys | Arg | Phe | Thr | Trp | Trp | Pro | |
| | | | | 165 | | | | | 170 | | | | | 175 | | |
| cag | atc | ttc | ctg | ggg | ctg | gcc | ttc | aac | tgg | ggc | gtc | atg | ctg | gcc | tat | 576 |
| Gln | Ile | Phe | Leu | Gly | Leu | Ala | Phe | Asn | Trp | Gly | Val | Met | Leu | Ala | Tyr | |
| | | | 180 | | | | | 185 | | | | | 190 | | | |
| gcc | gcg | cat | gcg | ggc | cgt | gtc | gat | gcg | gcc | cct | gtc | gtg | gca | tgg | ctg | 624 |
| Ala | Ala | His | Ala | Gly | Arg | Val | Asp | Ala | Ala | Pro | Val | Val | Ala | Trp | Leu | |
| | | 195 | | | | | 200 | | | | | 205 | | | | |
| ggg | gcc | atc | gcc | tgg | acg | atc | ttc | tac | gac | acc | acc | tat | gcc | cac | cag | 672 |
| Gly | Ala | Ile | Ala | Trp | Thr | Ile | Phe | Tyr | Asp | Thr | Thr | Tyr | Ala | His | Gln | |
| | 210 | | | | | 215 | | | | | 220 | | | | | |
| gac | gcc | gag | gac | gac | gcc | ctg | atc | ggg | gtg | aaa | tcc | acc | gcg | cgg | ctg | 720 |
| Asp | Ala | Glu | Asp | Asp | Ala | Leu | Ile | Gly | Val | Lys | Ser | Thr | Ala | Arg | Leu | |
| 225 | | | | | 230 | | | | | 235 | | | | | 240 | |
| ttc | ggc | gac | aaa | agc | ccg | cgc | atc | ctt | gcg | gga | ttc | gcc | ctg | ggc | gcg | 768 |
| Phe | Gly | Asp | Lys | Ser | Pro | Arg | Ile | Leu | Ala | Gly | Phe | Ala | Leu | Gly | Ala | |
| | | | | 245 | | | | | 250 | | | | | 255 | | |
| gtc | ctg | gtg | ctg | atg | ctg | gcc | acc | gcg | ctg | ccc | ggt | cgc | aat | ctg | ttg | 816 |
| Val | Leu | Val | Leu | Met | Leu | Ala | Thr | Ala | Leu | Pro | Gly | Arg | Asn | Leu | Leu | |
| | | | 260 | | | | | 265 | | | | | 270 | | | |
| att | gcc | tgg | gcg | ggc | gtc | gcg | ggt | ttc | ggc | ctg | cac | cta | ggc | tgg | cag | 864 |
| Ile | Ala | Trp | Ala | Gly | Val | Ala | Gly | Phe | Gly | Leu | His | Leu | Gly | Trp | Gln | |
| | | 275 | | | | | 280 | | | | | 285 | | | | |
| ctt | cgc | aaa | ttc | cag | ccg | gat | cag | ggc | gat | acc | tgc | ctg | cgc | ctg | ttc | 912 |
| Leu | Arg | Lys | Phe | Gln | Pro | Asp | Gln | Gly | Asp | Thr | Cys | Leu | Arg | Leu | Phe | |
| | 290 | | | | | 295 | | | | | 300 | | | | | |

```
cgg tcc aac cgc gat gcg ggg ctg atc ctt gcg ctg ttt ctt gcc gtg      960
Arg Ser Asn Arg Asp Ala Gly Leu Ile Leu Ala Leu Phe Leu Ala Val
305                 310                 315                 320 gcg ggc ctc gca tga                                                  975
Ala Gly Leu Ala
```

<210> SEQ ID NO 24
<211> LENGTH: 324
<212> TYPE: PRT
<213> ORGANISM: Paracoccus zeaxanthinifaciens

<400> SEQUENCE: 24

```
Met Asn Asn Arg Ile Phe Ala Met Met Gly Asn Ala Met Gln Ser Ser
1               5                   10                  15

Thr Glu Arg Pro Asp Ala Val Val Asp Ala Pro Lys Gly Asn Trp Val
            20                  25                  30

Asp Glu Ile Ala Pro Pro Trp Ser Arg Pro Trp Leu Arg Leu Ser Arg
        35                  40                  45

Ala Asp Arg Pro Ile Gly Thr Trp Leu Leu Leu Leu Pro Cys Trp Trp
    50                  55                  60

Gly Ile Gly Leu Ala Met Met Ala Asp Gly Pro Arg Trp Phe Asp Ala
65                  70                  75                  80

Trp Ile Ala Leu Ala Cys Thr Ile Gly Ala Phe Val Met Arg Gly Ala
                85                  90                  95

Gly Cys Thr Trp Asn Asp Ile Thr Asp Arg Arg Ile Asp Ala Gln Val
            100                 105                 110

Ala Arg Thr Arg Ser Arg Pro Leu Pro Ser Gly Gln Val Thr Leu Arg
        115                 120                 125

Gly Ala Tyr Gly Trp Leu Ile Ala Gln Gly Leu Ile Gly Leu Ala Ile
    130                 135                 140

Leu Leu Thr Leu Gly Gln Ala Ala Ile Trp Met Gly Val Ala Ser Leu
145                 150                 155                 160

Ala Leu Val Ala Ile Tyr Pro Phe Ala Lys Arg Phe Thr Trp Trp Pro
                165                 170                 175

Gln Ile Phe Leu Gly Leu Ala Phe Asn Trp Gly Val Met Leu Ala Tyr
            180                 185                 190

Ala Ala His Ala Gly Arg Val Asp Ala Ala Pro Val Val Ala Trp Leu
        195                 200                 205

Gly Ala Ile Ala Trp Thr Ile Phe Tyr Asp Thr Thr Tyr Ala His Gln
    210                 215                 220

Asp Ala Glu Asp Ala Leu Ile Gly Val Lys Ser Thr Ala Arg Leu
225                 230                 235                 240

Phe Gly Asp Lys Ser Pro Arg Ile Leu Ala Gly Phe Ala Leu Gly Ala
                245                 250                 255

Val Leu Val Leu Met Leu Ala Thr Ala Leu Pro Gly Arg Asn Leu Leu
            260                 265                 270

Ile Ala Trp Ala Gly Val Ala Gly Phe Gly Leu His Leu Gly Trp Gln
        275                 280                 285

Leu Arg Lys Phe Gln Pro Asp Gln Gly Asp Thr Cys Leu Arg Leu Phe
    290                 295                 300

Arg Ser Asn Arg Asp Ala Gly Leu Ile Leu Ala Leu Phe Leu Ala Val
305                 310                 315                 320

Ala Gly Leu Ala
```